(12) United States Patent
Simpson

(10) Patent No.: US 10,208,665 B2
(45) Date of Patent: Feb. 19, 2019

(54) METHODS AND SYSTEMS FOR ENERGY CONVERSION AND GENERATION

(71) Applicant: THERMOGAS DYNAMICS LIMITED, Largs, Ayrshire (GB)

(72) Inventor: Robert Simpson, Largs (GB)

(73) Assignee: Thermogas Dynamics Limited, Largs, Ayrshire (GB)

( * ) Notice: Subject to any disclaimer, the term of this patent is extended or adjusted under 35 U.S.C. 154(b) by 852 days.

(21) Appl. No.: 14/379,946

(22) PCT Filed: Feb. 18, 2013

(86) PCT No.: PCT/GB2013/050375
§ 371 (c)(1),
(2) Date: Aug. 20, 2014

(87) PCT Pub. No.: WO2013/124632
PCT Pub. Date: Aug. 29, 2013

(65) Prior Publication Data
US 2016/0017800 A1    Jan. 21, 2016

(30) Foreign Application Priority Data
Feb. 20, 2012    (GB) .................................. 1202791.8

(51) Int. Cl.
C07C 1/12 (2006.01)
C07C 9/04 (2006.01)
(Continued)

(52) U.S. Cl.
CPC .................. *F02C 3/22* (2013.01); *C07C 1/12* (2013.01); *C10G 2/50* (2013.01); *C10G 50/00* (2013.01);
(Continued)

(58) Field of Classification Search
CPC ....................................................... C25B 1/10
See application file for complete search history.

(56) References Cited

U.S. PATENT DOCUMENTS 4,452,676 A    6/1984    Birbara
5,128,003 A    7/1992    Murdoch
(Continued)

FOREIGN PATENT DOCUMENTS

CN    102116585    7/2011
DE    4332789    3/1995
(Continued)

OTHER PUBLICATIONS

International Search Report & Written Opinion for PCT/GB2013/050375, dated Aug. 23, 2013.
(Continued)

*Primary Examiner* — Nicholas A Smith
(74) *Attorney, Agent, or Firm* — Dickinson Wright PLLC; Christopher A. Mitchell

(57) ABSTRACT

The invention relates to methods and systems of converting electrical energy to chemical energy and optionally reconverting it to produce electricity as required. In preferred embodiments the source of electrical energy is at least partially from renewable source. The present invention allows for convenient energy conversion and generation without the atmospheric release of CO2. One method for producing methane comprises electrolysis of water to form hydrogen and oxygen, and using the hydrogen to hydrogenate carbon dioxide to form methane. It preferred to use the heat produced in the hydrogenation reaction to heat the water prior to electrolysis. The preferred electrical energy source for the electrolysis is a renewable energy source such as solar, wind, tidal, wave, hydro or geothermal energy. The method allows to store the energy gained at times of low demand in the form of methane which can be stored and
(Continued)

used to generate more energy during times of high energy demand. A system comprising an electrolysis apparatus and a hydrogenation apparatus, and a pipeline for the transportation of two fluids, is also described.

4 Claims, 9 Drawing Sheets

(51) Int. Cl.
| | |
|---|---|
| C10G 2/00 | (2006.01) |
| C25B 1/04 | (2006.01) |
| C25B 1/06 | (2006.01) |
| C25B 1/10 | (2006.01) |
| C25B 9/18 | (2006.01) |
| F02C 3/22 | (2006.01) |
| B01D 53/62 | (2006.01) |
| C10G 50/00 | (2006.01) |
| C25B 15/02 | (2006.01) |
| F01K 13/00 | (2006.01) |
| F01K 19/00 | (2006.01) |
| H01M 8/0656 | (2016.01) |

(52) U.S. Cl.
CPC .............. *C25B 1/04* (2013.01); *C25B 1/06* (2013.01); *C25B 1/10* (2013.01); *C25B 9/18* (2013.01); *C25B 15/02* (2013.01); *F01K 13/00* (2013.01); *F01K 19/00* (2013.01); *H01M 8/0656* (2013.01); *B01D 53/62* (2013.01); *C07C 2521/04* (2013.01); *C07C 2523/46* (2013.01); *Y02E 20/16* (2013.01); *Y02E 20/326* (2013.01); *Y02E 20/344* (2013.01); *Y02E 60/34* (2013.01); *Y02E 60/366* (2013.01); *Y02E 70/10* (2013.01); *Y02P 20/129* (2015.11); *Y02P 20/133* (2015.11); *Y02P 20/134* (2015.11); *Y02P 20/582* (2015.11)

(56) References Cited

U.S. PATENT DOCUMENTS

| | | | |
|---|---|---|---|
| 5,711,770 | A | 1/1998 | Malina |
| 7,364,810 | B2 * | 4/2008 | Sridhar ............. H01M 8/04201 429/418 |
| 8,278,362 | B2 | 10/2012 | Wiesner |
| 2008/0245660 | A1 | 10/2008 | Little et al. |
| 2009/0139874 | A1 * | 6/2009 | Peter ......................... C25B 1/02 205/349 |
| 2009/0289227 | A1 | 11/2009 | Rising |
| 2010/0300892 | A1 | 12/2010 | Matare et al. |
| 2011/0041740 | A1 * | 2/2011 | Reilly ....................... F23C 9/00 110/341 |
| 2011/0042228 | A1 * | 2/2011 | Hinatsu ..................... C25B 1/10 205/344 |
| 2013/0108939 | A1 * | 5/2013 | Besse ........................ C25B 1/12 429/422 |
| 2014/0291162 | A1 * | 10/2014 | Sala ........................ C25B 15/00 205/446 |

FOREIGN PATENT DOCUMENTS

| | | |
|---|---|---|
| DE | 4332790 | 3/1995 |
| DE | 102007037672 | 2/2009 |
| EP | 0497226 | 8/1992 |
| EP | 0539224 | 4/1993 |
| EP | 2100869 | 9/2009 |
| GB | 2459430 | 10/2009 |
| JP | 2009120900 | 6/2009 |
| JP | 2009131835 | 6/2009 |
| JP | 2011208242 | 10/2011 |
| WO | WO0025380 | 5/2000 |
| WO | WO2008012039 | 1/2008 |
| WO | WO2011020825 | 4/2011 |
| WO | WO 2011131622 A1 * | 10/2011 ............... C25B 1/12 |
| WO | 2012003849 | 1/2012 |
| WO | WO2012028326 | 3/2012 |

OTHER PUBLICATIONS

Great Britain Search Report under Section 17 for GB1202791.8, Jun. 19, 2012.
Nano Letters, vol. 9, Varghese et al, High-rate solar photcatalytic conversion of CO2 and water vapour to hydrocarbon fuels, p. 731-737.
Anderson et al, "Adapting Gas Turbines to Zero Emission Oxy-Fuel Power Plants," Proceedings of ASME Turbo Expo 2008: Power for Land, Sea and Air GT, 2008, pp. 1-11.
Hashimoto et al, "Carbon dioxide, the feedstock for using renewable energy," Symposium A, E-MRS 2010 Fall Meeting, IPO Conf. Series: Materials Science and Eng'g, 2010, pp. 1-14, vol. 19.
Alstom Carrington, "Carrington Power is an exciting new electricity generation project befing built in Carrington Greater Manchester . . .," URL:carringtonpowerconstruction.co.uk, Date of publication unknown, Accessed Jun. 4, 2015.
CHP ASS'N "Uses of CHP," URL:chpassociation.org/uses-of-chp/, Date of publication unknown, Accessed Jul. 8, 2015.
Drakelow Combine Cycle Gas Turbine Power Station Extension, Derbyshire (UK), "Environmental Statement," Apr. 2009.
EEA, "Air pollution from electricity-generating large combustion plants," Technical Report, No. 4/2008 (2008).
Doctor et al, "High-Temperature Electrolysis," DOE Solar-Hydrogen Workshop, Argonne National Laboratory, Nov. 9-10, 2004.
Richardson, "Improved Sabatier Reactions for In Situ Resource Utilization on Mars Missions," UHCL/UH, 1999-2000, pp. 84-86.
"Method of combining existing chemical processes to produce hydrocarbon fuels," URL: www.google.com/patents/US8278362, Publication date unknown, Accessed Jun. 6, 2015.
OCMOL, "OCMOL Process," URL:www.ocmol.eu/index.php, Publication date unknown, Accessed Jun. 4, 2015.
Cheng-Chieh Chao, "Surface Modification of Yttria-Stabilized Zirconia Electrolyte by Atomic Layer Deposition," Nano Letters, 2009, pp. 3626-3628, vol. 9, Issue 10.
Jaso et al., "20th European Symposium on Computer Aided Process Engineering, Oxidative Coupling of Methane: Reactor Performance and Operating Conditions" 20th European Symposium on Computer Aided Process Engineering, 2010.
Siemens Clean Energy Systems, "Oxy Fuel Turbine Technology Development Program Overview" (Publication date unknown).
US Doe, National Energy Technology Laboratory, "Oxy-Fuel Combustion" (Publication date unknown).
Asia Industrial Gases Ass'n, "Oxygen Pipeline Systems," AIGA 021/05, 2005, pp. 1-3.
Royal Academy of Eng'g, "Can we afford to keep the lights on? Real future electricity costs," Mar. 10, 2004.
Wikipedia, "Sabatier Reaction," URL:en.wikipedia.org/wiki/Sabatier_reaction (Publication date unknown) (Accessed Jun. 2, 2015).
Bloomberg, "Samsung to Deliver World's Biggest LNG Tanker for Exxon Project," (Jul. 7, 2008), URL:www.bloomberg.com/apps/news?pid=newsarchive$sid=ayn7XSw1Ktg4.
Dry, "The Fischer-Tropsch Process: 1950-2000," Catalysis Today, 2002, 227-241, vol. 71.
ABC, URL:www.abc.net.au/radionational/programs/scienceshow/using-solar-power-to-produce-non-fossil-liquid/2990876 (Mar. 5, 2011)(Accessed Jun. 1, 2015).
S H Salter et al., "Vertical-axis tidal-current generators and the Pentland Firth," Proc.1MechE, Mar. 1, 2007,pp. 181-185, vol. 221 Part A: J. Power and Energy.

* cited by examiner

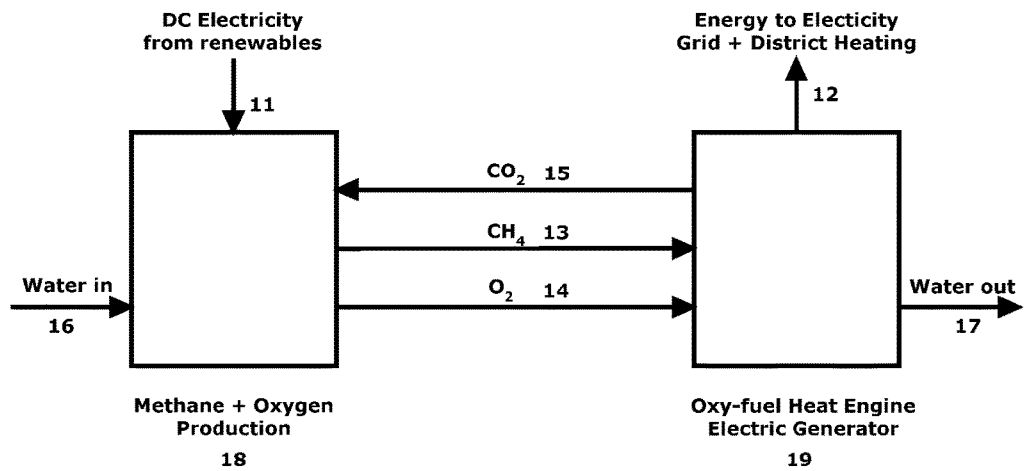
Figure 1a. Energy Transference
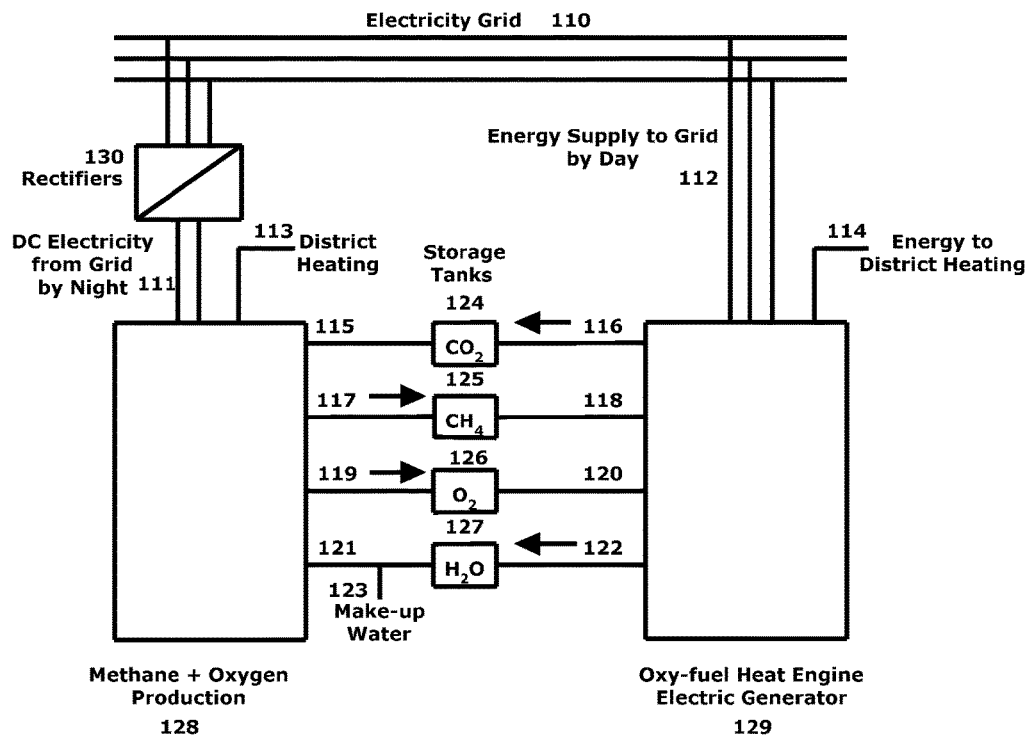
Figure 1b. Time Phased Energy Transference

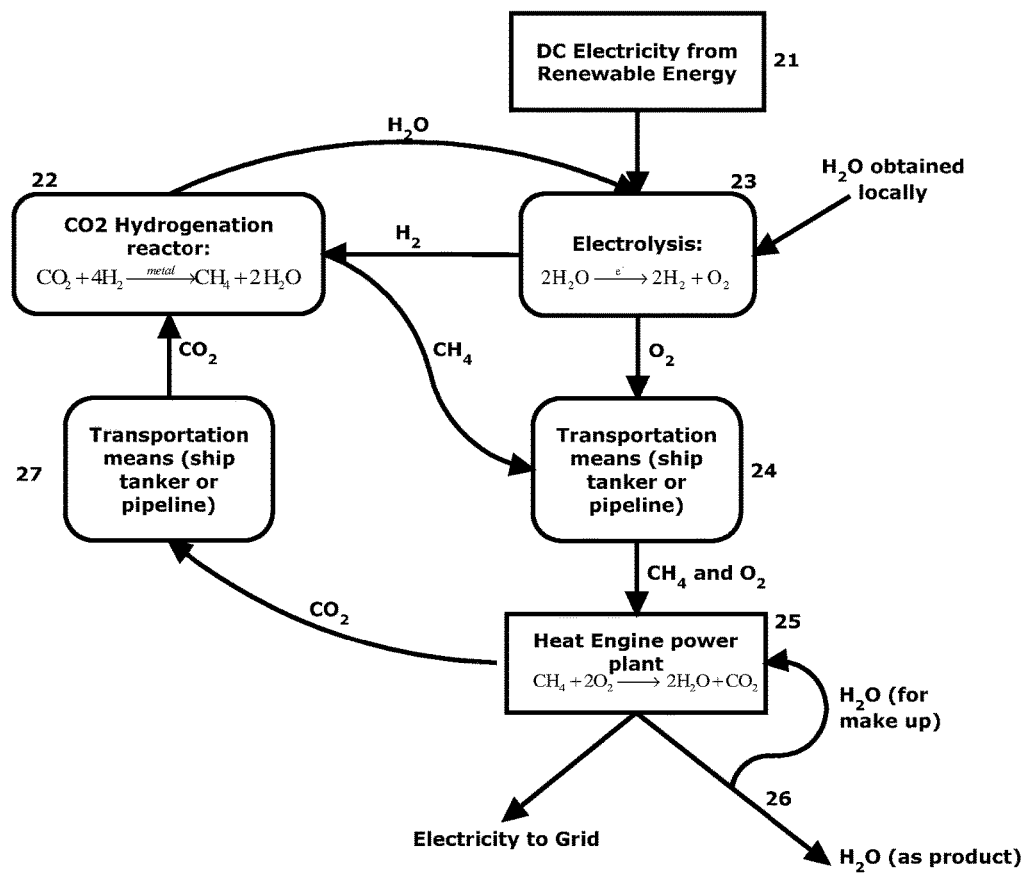
Figure 2. Flowchart showing a General Outline of the Method

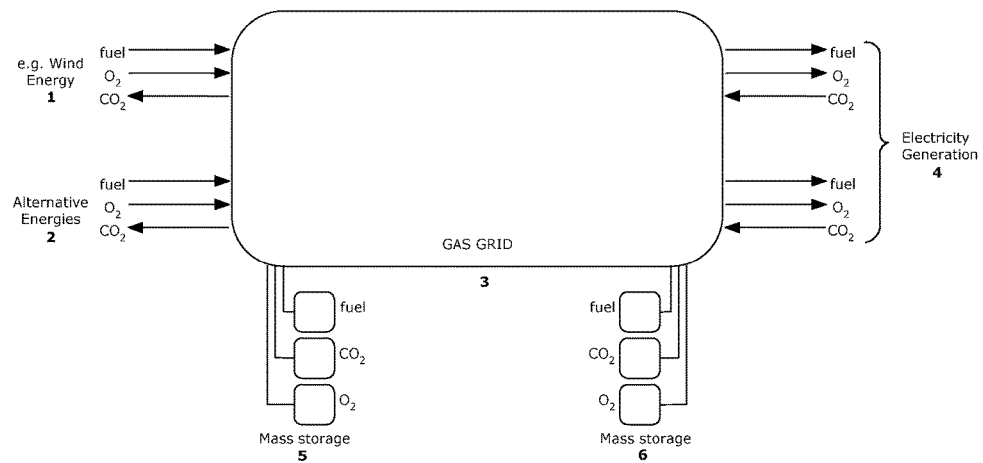
Figure 4a. Schematic showing inputs, take-offs and storage capabilities.
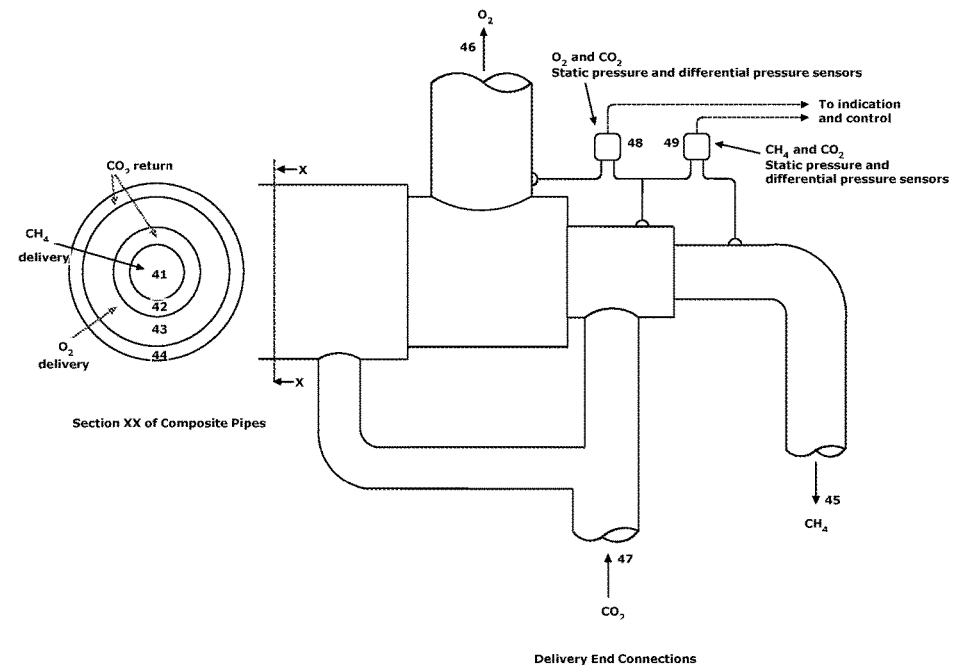
Figure 4b. Possible Composite Pipework for Commodities Transfer

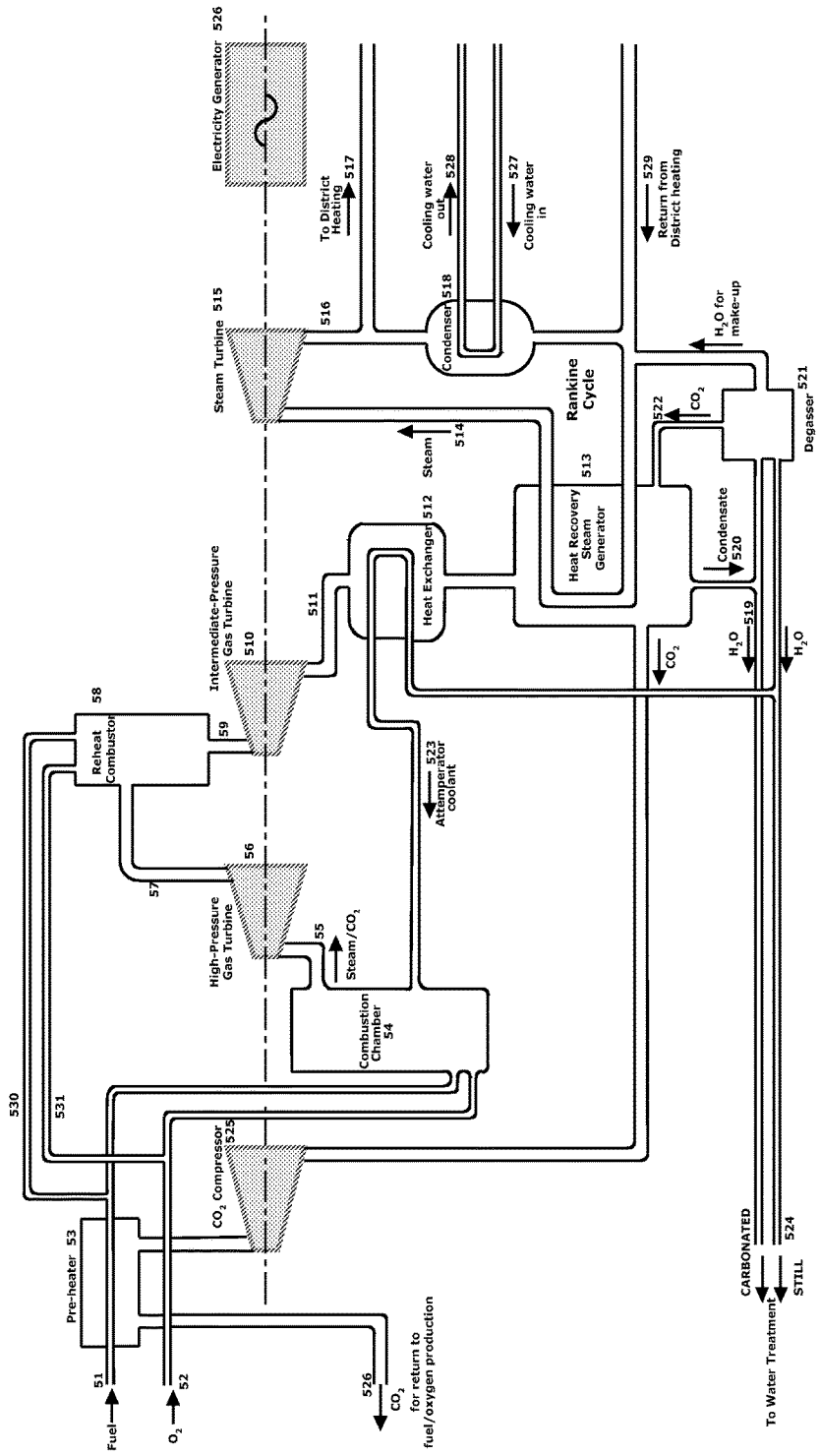
Figure 5. Combined Cycle Oxy-Fuel Gas Turbine Generator with $CO_2$ Recovery.

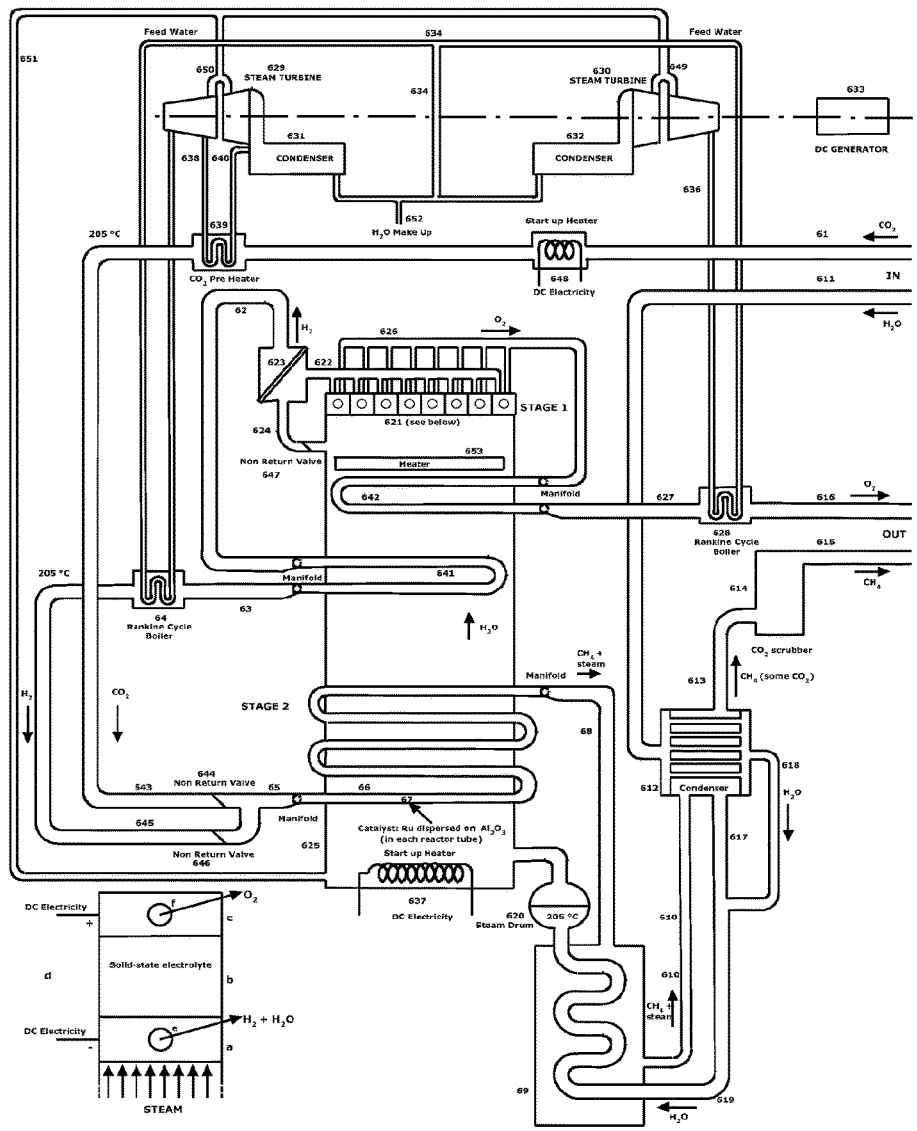
Figure 6a. Electrolysis Cell 621.
Figure 6. Combined Two-stage Fuel and Oxygen Production Recovering Heat from Product Gasses with Electricity Generation for Further Product Production

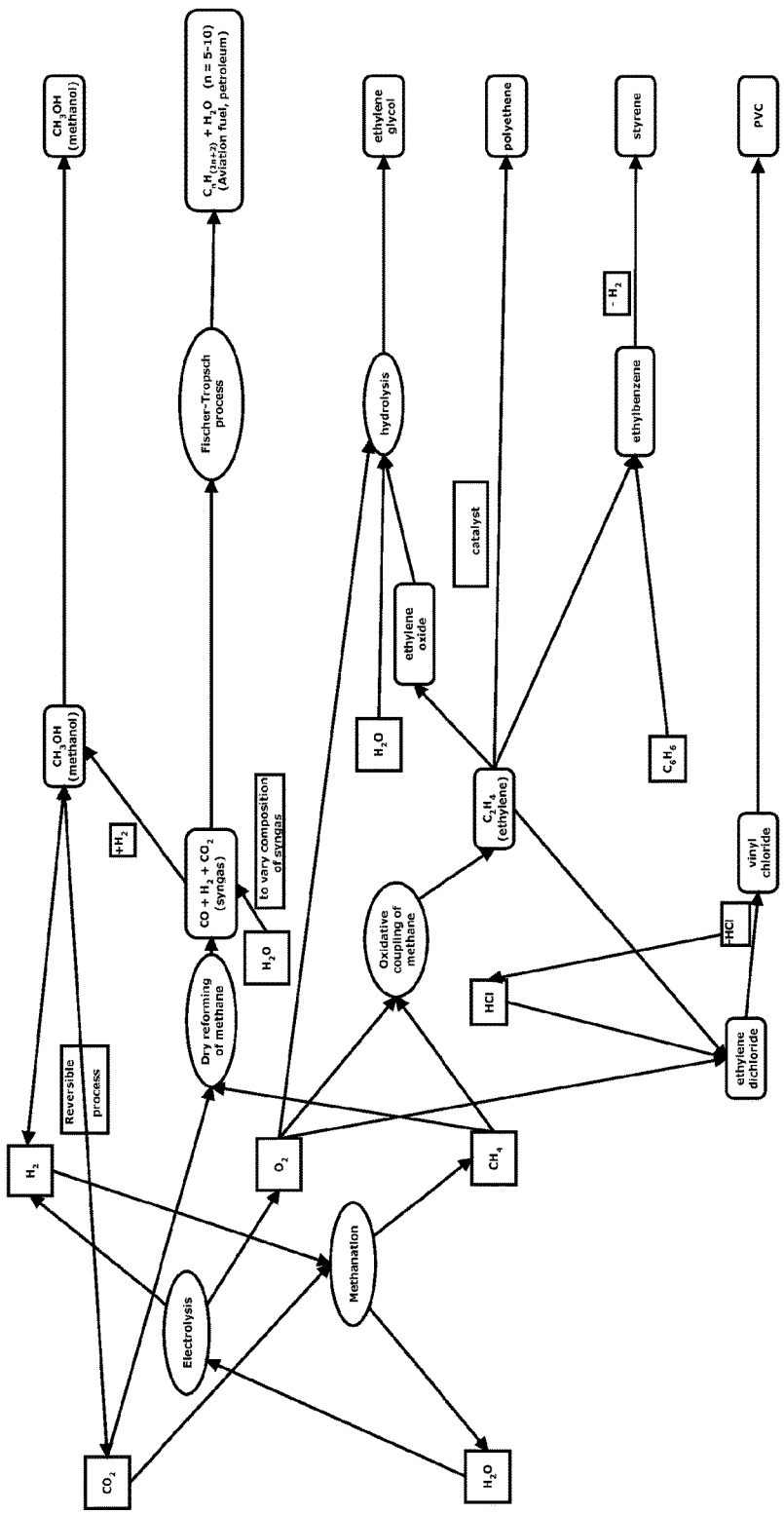
Figure 8 Synthesis Chart

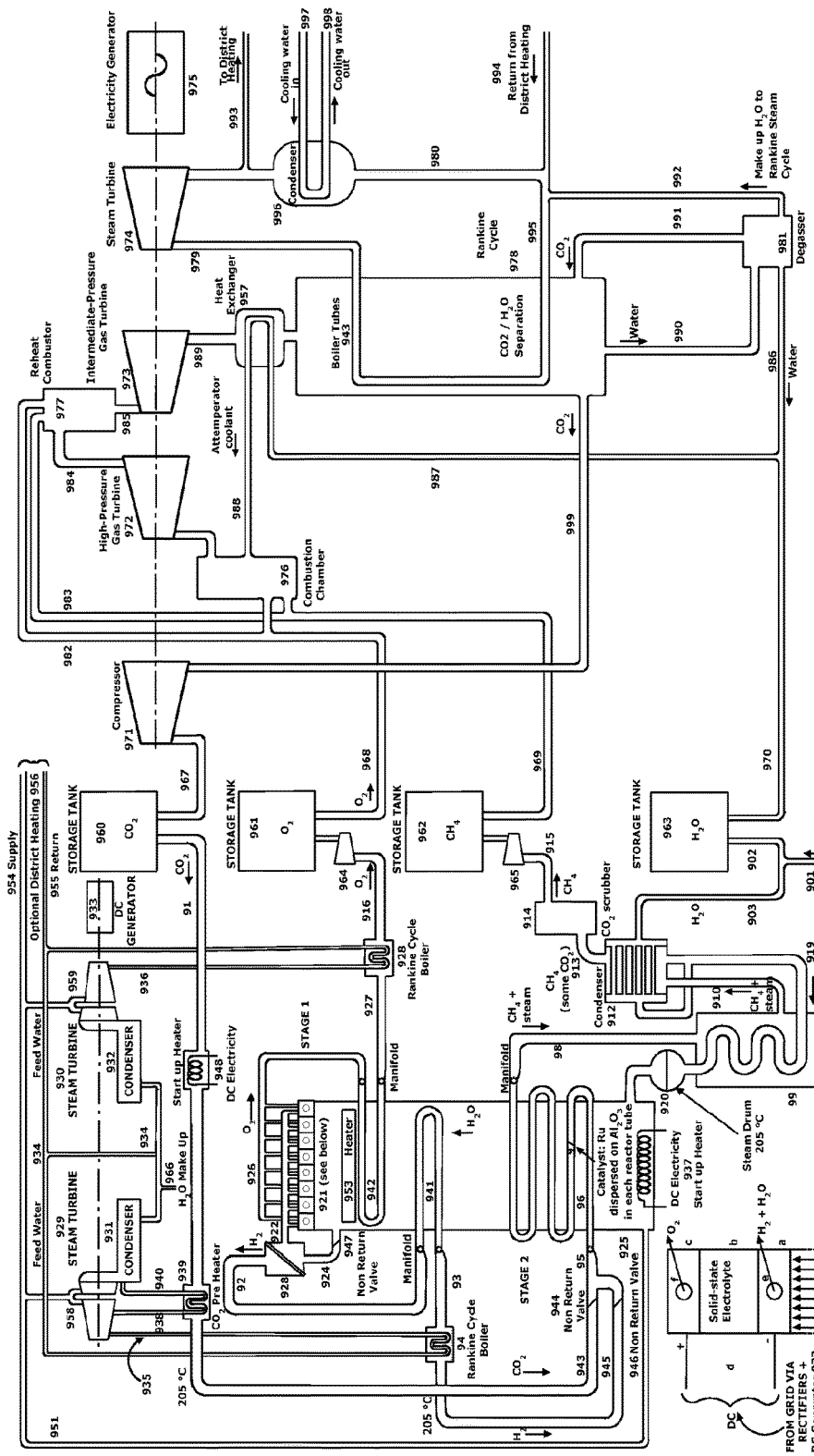

METHODS AND SYSTEMS FOR ENERGY CONVERSION AND GENERATION

The present application is a 35 U.S.C. Section 371 national stage filing of International Patent Application No. PCT/GB2013/050375, filed 18 Feb. 2013, and through which priority is claimed to UK application GB 1202791.8, filed 20 Feb. 2012, the disclosures of which are incorporated herein by reference in their entireties.

This present invention relates to improved methods and systems of converting electrical energy to chemical energy, and optionally converting the chemical energy back to electrical energy and thereby providing electrical energy when required. The present invention provides highly efficient methods and systems for making combustible fuel or petrochemical feed stock from electrical energy, wherein the electrical energy may, in certain embodiments, be provided by non-fossil fuel energy and associated technologies. In an alternative embodiments the present invention may be used for converting electrical energy to chemical energy at certain times (e.g. of relatively low demand or price), for subsequent conversion to electrical energy at other times (e.g. where demand or price is high). The present invention can involve a recurrent process of energy transference for use in the supply of emissions-free electricity, and optionally district heating and a source of water for drinking or other purposes.

BACKGROUND

The continuing drive to meet the ever-expanding energy requirements of a burgeoning global population is proving to be one of the biggest challenges facing mankind in the early $21^{st}$ century. The basic means of energy supply has remained largely unchanged since the dawn of large-scale generation: combustion of fossil fuels such as coal, oil and natural gas still provides the vast majority of electricity, both in the United Kingdom and worldwide. Since the 1960s, however, there has been growing concern about what effect one of the principal products of this combustion, carbon dioxide ($CO_2$), is having on the climate of our world. Climate scientists are now in near-universal agreement that our continued reliance on fossil fuel combustion is increasing the levels of atmospheric $CO_2$ at a rate that will cause a substantial warming of our planet if left unchecked.

Reliance upon fossil fuels for the majority of electricity generation, transport and domestic heating or cooling has pushed the levels of the greenhouse gas carbon dioxide ($CO_2$) ever upward. Climate scientists may be correct when they attribute global warming to the escalating levels of $CO_2$ in the atmosphere. Atmospheric $CO_2$ levels rose from 300 ppm to 370 ppm in the $20^{th}$ Century. As the fossil fuel burn continues the risk of rising global temperatures leading to a runaway effect is greatly feared.

International agreements to reduce $CO_2$ emissions have stalled against the lack of resolve to institute measures to achieve proposed percentage reductions. Moreover agreements to cut amounts of $CO_2$ which if implemented would still not stop escalating $CO_2$ levels in the atmosphere are not an adequate solution and this only goes to illustrate the scale of the problem. In contrast, universal adoption of the present invention would completely prevent emissions from electricity supply, with the potential for saving of the order of 14 GTonnes per year of $CO_2$ from entering the atmosphere compared to the International Energy Agency's total account of all emissions from primary fuel combustion globally in 2010 of 30.6 GTonnes per year of $CO_2$.

Currently fossil fuel electricity generating stations release the $CO_2$ formed during combustion into the atmosphere, although there are some pilot studies into $CO_2$ extraction and sequestration, such as at Longannet in Fife, UK. Damage to human health and to eco-systems caused by the pollution of the atmosphere resulting from the combustion of fossil fuels is widely acknowledged. Current technology is inadequate to prevent the damage caused by sulphurous, nitrogenous and particulate pollution of the atmosphere.

Immediate and decisive action is now required on an international scale in order to arrest this rise in atmospheric $CO_2$ before global temperatures increase to levels that will cause severe changes to our environment. Consequently, the search for less polluting ('greener') methods of energy generation has gathered pace significantly. Research has focused on two key areas:

the capture of the $CO_2$ produced in fossil-fuel combustion, generally for sequestration; and effective means for harnessing the vast reserves of energy evidently inherent in nature—so-called renewable energy.

$CO_2$ recovery ('carbon-capture') methods are increasingly attracting large-scale investment, with governments encouraging their development by providing financial incentives to oil and gas multinationals. For example "clean coal technology" is based upon $CO_2$ extraction from the flue gasses and then sequestration by insertion into gas or oil well geological structures. However, the separation of $CO_2$ from the flue gases at a conventional hydrocarbon-fired power plant, while practicable, has two main drawbacks. Firstly, it results in a large drop in efficiency (and therefore profitability) of the plant, due to the recovery process. Secondly, and importantly, there are no guarantees that sequestered $CO_2$ will not, over time, escape from its geological prison and make its way into the atmosphere. Improvements to the ease of $CO_2$ recovery are emerging, notably through investigating the potential to combust the hydrocarbon fuel in $O_2$ rather than air—'oxyfuel combustion,' as will be elaborated upon later.[1]

It is self-evident that direct electricity generation from renewable energy sources, such as wind, tidal and solar power, amongst others, represent the greenest method of all, since no $CO_2$ is emitted in this way. However, politicians and the energy industry are naturally reluctant to gamble on a large-scale switch-over to renewable energy sources, while the technology to harness these effectively and reliably remains in its infancy. Many of the most promising sources of renewable energy are plagued by unpredictability. For example, wind turbines generate very intermittently and unreliably, their output being dependent on a constantly-changing force, the strength and direction of the wind at any point in time. Nuclear power, the only large-scale alternative to fossil fuel combustion currently in use, represents the other end of the scale: it is very inflexible, generating at a constant output level and thus poorly placed to respond to sudden peaks or dips in electricity demand, which are common. Since electricity must be used as it is produced, both flexibility and reliability are required in an efficient generating system.

Accordingly, much study has been done into the possibility of converting electricity into other forms of energy, for storage and use to meet subsequent demand. One popular area of study is into the manufacture of combustible gases from alternative energy sources. For example, research has been done both in the United States[2] and in Japan[3] into the possibility of producing methane from solar energy, with a pilot plant being established in the latter case to demonstrate its feasibility.

The present invention provides improved methods of capturing and storing electrical energy, optionally from renewable sources, but also from conventional generation technologies. It also provides a fully-integrated approach to energy storage and generation without the emission of $CO_2$ to the atmosphere. The present invention will describe means to produce electricity reliably when required and local to the demand.

STATEMENTS OF THE INVENTION

In a first aspect the present invention provides a method for producing a hydrocarbon or a hydrocarbon derivative from an electrical energy source, said method comprising;
 a) using electrical energy from said source to lyse (e.g. electrolyse) water to form hydrogen and oxygen; and
 b) using hydrogen thereby formed to hydrogenate carbon dioxide to form methane.

In a preferred embodiment the electrical energy is obtained by operating a non-fossil fuel energy generator to obtain electrical energy from a non-fossil fuel energy source. The energy thereby obtained is used to lyse water. It should be born in mind that water can be in liquid form or can be in gaseous form, i.e. as steam.

In another embodiment the electrical energy can be taken from an existing electricity grid, suitably at periods of low demand/cost for electricity, e.g. during the night. This allows the present invention to act as a buffer when demand for electricity is low, converting electrical energy to hydrocarbons or hydrocarbon derivatives.

One significant advantage of the present invention is that it allows for storage of electricity produced by generators that cannot vary generation of electricity on demand. This is the case with most renewable or non-fossil fuel energy sources which cannot be controlled and/or predicted, and nuclear power which is comparatively inflexible. Indeed, it is often inconvenient and/or inefficient to vary production from many current fossil fuel electricity generation facilities.

It is primarily envisaged that the electricity will be used to electrolyse water, preferably at high temperature and/or pressure. However, it is possible that the electricity may be used to heat the water up to achieve thermolysis. Thermolysis occurs at high temperatures, e.g. 2000° C. or higher, and thus suitable materials for building a suitable apparatus remains an issue. However, research in this area is continuing and in certain situations it may become a suitable approach. Where electrolysis is mentioned in the following text, it should be borne in mind that other water lysing methods which can use electricity are contemplated.

The method may comprise the step of further processing said methane to form hydrocarbons other than methane, or hydrocarbon derivatives. The term "hydrocarbon derivatives" is used to refer to chemical compounds which are largely made up of carbon and hydrogen, and which can be derived from methane, but which contain additional elements (e.g. oxygen, nitrogen or halogens), such as carbohydrates, alcohols, carboxylic acids, amines, amides etc. This is described in more detail below.

Preferably the non-fossil fuel energy source is one or more of wind energy, tidal energy, wave energy, hydro energy, geothermal energy, solar energy and nuclear energy. It is most preferred that the energy source is a renewable energy source, i.e. excluding nuclear from the above list. It should be noted that the term renewable is used as an umbrella term for 'green', non-fossil fuel-based energy, as it typical in the art, even if strictly speaking all sources of energy are finite. Suitable non-fossil generation means that are adapted to derive electrical power from such renewable energy sources are well known in the art, and moreover technologies in this area are rapidly developing and there is a considerable political and environmental drive to generate more electricity from such sources in place of fossil fuel-based generation. For example, hydroelectric generation has long been carried out on both local and massive scales, wind generation by wind turbines in both onshore and offshore environments is a relatively well established technology, and tidal generation is rapidly becoming a reality. A detailed discussion of the relevant generation means is therefore not required.

In order to conduct electrolysis of water a direct electrical current is generally preferred. DC generators or rectifiers can be used to obtain a direct current from an alternating current, e.g. as produced by such renewable energy generators or from the grid.

The electrolysis is preferably carried out in an electrolysis apparatus. There has been a significant amount of work in developing systems for high efficiency electrolysis, and such systems would be readily applied to the present invention. For example, in certain embodiments it is preferred that electrolysis is performed at an elevated temperature, relative to ambient. Increased temperature has been shown to improve efficiency (such systems are often termed High-Temperature Electrolysis or Steam Electrolysis).

Accordingly the method preferably involves heating the electrolysis reaction to a desired temperature. In particular it is preferred that electrolysis is carried out at 100° C. to 1000° C., more preferably from 250° C. to 950° C., especially from 800° C. to 925° C.

Additionally, or alternatively, it is preferred that a solid oxide electrolyser system is used; such systems have been shown to offer increased efficiency. In particular, the use of yttria-stabilised zirconia ('YSZ', $Y_2O_3$ in $ZrO_2$), a gastight electrolyte which conducts $O^{2-}$ ions well at high temperatures, greatly facilitates separation of the hydrogen and oxygen products.

Preferred electrodes are nickel-cermet steam/hydrogen electrodes.

The gaseous products oxygen and hydrogen are obtained as a product of electrolysis and typically obtained, and optionally stored, separately for future use. Hydrogen and oxygen are both potentially dangerous chemicals due to their high reactivity, but techniques for their safe storage and manipulation are well known in the art.

Hydrogenation of carbon dioxide to methane is suitably carried out in the so-called Sabatier process, wherein the reaction can be summarised as follows:

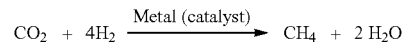

$$CO_2 + 4H_2 \xrightarrow{\text{Metal (catalyst)}} CH_4 + 2H_2O$$

This process is relatively well known, and suitable methods and apparatus to carry out said reaction are readily available to the skilled person.

The Sabatier process is exothermic, and thus there is typically a need to cool the reaction system. If the reaction temperature significantly exceeds 300° C. there is a loss in efficiency as the back reaction becomes favoured, thus it is preferred that the temperature is kept around 300° C. A preferred temperature range is from 200° C. to 400° C., more preferably from 250° C. to 350° C., especially from 275° C. to 325° C. This can be achieved by cooling, e.g. using a liquid or gas based cooling system, e.g. water or steam circulated in a heat exchanger, which is thermally coupled to the reaction system. Accordingly, it is typically preferred that the method involves cooling the hydrogenation reaction. In a preferred embodiment of the invention, water surrounding at least a portion of the hydrogenation reactor, and thus cooling it, is used as a feedstock for the electrolysis reaction.

It is preferred that the metal catalyst for the Sabatier process comprises Ru on $Al_2O_3$. This catalyst provides good selectivity and a large surface area for reaction within a small reactor volume, which is well suited to the present invention. Alternative catalysts (e.g. nickel) will be apparent to the person skilled in the art, and it is expected that this reaction will be the subject of technological developments in the coming years—such developments could readily be used in the present invention.

In a preferred embodiment of the present invention, excess heat produced by the hydrogenation of carbon dioxide (which may be removed from the hydrogenation system by the cooling system) is used to heat the electrolysis reaction. This allows heat from the hydrogenation reaction to be re-used, thus improving efficiency of the electrolysis reaction. The excess heat can suitably be used to heat the input water for the electrolysis process prior to or during electrolysis.

In a preferred embodiment of the invention, at least a portion the output of the electrolysis reaction (i.e. high temperature hydrogen and/or oxygen) is used to heat the electrolysis reaction, e.g. the input water. This allows heat energy contained in the output to be used to increase efficiency of the electrolysis process.

In certain preferred embodiments of the present invention residual heat in the oxygen and/or the hydrogen produced by electrolysis is used to drive generation of electricity. Such electricity can suitably be used to drive electrolysis. Even after the oxygen and/or hydrogen has been used to heat the input water for electrolysis, it will typically be at high temperature. Rather than waste this energy, it can be used to drive electricity generation through a suitable electricity generator. Suitably the oxygen and/or hydrogen is used to drive a boiler, e.g. a Rankine cycle boiler, to drive a steam turbine. This approach to maximise efficiency can be carried out whether or not the hydrogen and/or oxygen is used to heat the input water.

In preferred embodiments the method comprises directing steam generated from said boilers as input water for electrolysis. This is particularly useful where it is desirable to retain the maximum amount of heat in the system, e.g. during start up. It allows the method to avoid excess energy loss, e.g. in condensers after the steam turbine, when it is desirable to retain this energy. This can suitably be achieved using one or more steam bridges, which comprise valves which are operable to divert steam from the high pressure side of a steam turbine into a conduit leading to the input water for electrolysis. The method thus provides elevated temperature input water for electrolysis, returning the heat to the system, rather than allow it to pass through the turbine and into a condenser. Once the system is operating at a desired level the steam can be directed through the steam turbine, e.g. by operating the steam bridges, and thereby electricity is generated.

Water produced as result of the hydrogenation of carbon dioxide can conveniently be separated from the methane, e.g. by condensation. Such water can suitably be used for subsequent electrolysis or used in other ways.

Carbon dioxide for use in the present invention can suitably be the waste product of the combustion of a fuel, e.g. in a fuel burned in electricity generation. Carbon dioxide sequestration is a rapidly evolving field, and the amount of carbon dioxide being captured which needs to be dealt with is likely to increase rapidly. The present invention provides a much-needed use for such carbon dioxide, and one which is much more attractive than current storage options. The ability to use the carbon dioxide product, and convert it into a useful product, i.e. methane or derivatives thereof, makes the present invention economically and environmentally highly attractive. In a preferred embodiment discussed further below, the carbon dioxide is preferably the product of downstream oxygenation of the hydrocarbon or hydrocarbon derivative produced by the present method. In such a situation it will be apparent that the method becomes 'carbon neutral'.

Optimisation of the conditions of the various reactions of the present invention is a routine matter for the person skilled in the art.

In certain embodiments the method is for producing a hydrocarbon fuel suitable for use in an electricity generator suitable for deriving electrical energy from said hydrocarbon fuel. Such a generator would typically be a combustion-based electricity generator or a fuel cell or a combined fuel cell and turbine. Combustion-based generators for use with various hydrocarbon based fuels are well known, and fuel cells are becoming an established technology. Various hybrid fuel-cell/turbine systems are also becoming available.

Preferably the hydrocarbon fuel is a gas. More preferably the fuel comprises methane, preferably at least 80% by volume methane, more preferably 90% or higher, 95% or higher, or 99% or higher methane.

Suitably the methane can be converted to methane hydrate, a solid which allows for convenient storage of methane in a low volume form.

A fuel comprising methane is particularly suitable for use in electricity generators adapted for use with natural gas. There are a range of generation technologies based around natural gas, and all would be potentially suitable. A particularly preferred electricity generator is a combined cycle gas turbine (CCGT).

In other embodiments of the present invention the methane produced by the hydrogenation of carbon dioxide can be used in formation of other hydrocarbons or hydrocarbon-based products, such as alkanes, alkenes, aldehydes, ketones, alcohols (mono-ols or polyols), and various polymeric precursors (monomers). Such downstream products can suitably be used as fuels, or may be used as petrochemical feedstuffs for chemical processes such a polymerisation. For example, the method may comprise subsequent formation of alkanols (e.g. methanol), alkanes (i.e. hydrocarbons of general formula $C_nH_{2n+2}$, wherein n=2 to 20, preferably wherein n=5 to 10, such as aviation fuel or petroleum), ethylene glycol, polyethylene, styrene, poly vinyl chloride (PVC). Methods of deriving such products, amongst others, from methane are known in the art and will not be discussed in detail here.

The method may optionally comprise obtaining, and optionally storing and/or transporting, oxygen from the electrolysis of water for later use in oxidation of said fuel, e.g. in combustion or in a fuel cell. This is discussed in more detail below.

In a second aspect the present invention provides a system for producing a hydrocarbon or a hydrocarbon derivative from an electrical energy source, said system comprising;
   a) a source of electrical energy;
   b) an electrolysis apparatus electrically coupled to said source of electrical energy which is operable to electrolyse water using the electrical energy to form hydrogen and oxygen;
   c) gas handling means to collect oxygen and hydrogen produced in said electrolysis apparatus; and
   d) a hydrogenation apparatus adapted to hydrogenate carbon dioxide to form methane using said hydrogen.

In certain embodiments it is preferred that the system comprises a non-fossil fuel energy generator operable to obtain electrical energy from a non-fossil fuel energy source, e.g. a renewable energy source, to which the electrolysis apparatus is electrically coupled. In alternative embodiments the source of electrical energy can be a connection to an electrical grid supplying electrical energy produced remotely.

Suitable types of non-fossil fuel energy generators are discussed above.

The system may further comprise means for converting AC electricity to DC. Such a means may be required when the electricity produced by the renewable energy generator is AC. Suitable means of obtaining a DC current include a DC generator or rectifier.

The electrolysis apparatus suitably comprises a reaction volume in which electrolysis can occur. Preferably the electrolysis apparatus comprises heating means adapted to heat the reaction volume above ambient temperature. In a preferred embodiment the heating means comprises a heat exchanger adapted to carry a fluid through the reaction volume or through the input water stream, allowing the transfer of heat energy from the fluid to the input water or reaction volume, thus increasing the temperature in the reaction volume. Alternatively or additionally water used to cool the hydrogenation reaction is used as a feedstock for the electrolysis reaction, which would already be at elevated temperature. In a preferred embodiment, tubes or other suitable conduits defining the hydrogenation reaction volume pass through the input water for the electrolysis reaction. Alternative or additional heating means would be apparent to the person skilled in the art, such as electrical heating means.

In a preferred embodiment conduits (e.g. tubes) for carrying at least a portion of the output of the electrolysis reaction are adapted to be in thermal communication with the input water for the electrolysis apparatus. For example, the tubes carrying at least one, other or both of the hydrogen and oxygen, as well as any non-lysed water present in said streams, pass through a vessel carrying the input water, and thus heat is transferred from the oxygen/hydrogen/water output of the electrolysis reaction to the input water. This has the advantage of increasing efficiency of electrolysis.

The hydrogenation apparatus preferably comprises a reaction volume within which hydrogenation can occur. Preferably the reaction volume is defined by a plurality of conduits (e.g. tubes). Preferably the hydrogenation apparatus comprises cooling means adapted to cool the reaction volume. In a one embodiment the cooling means comprises a heat exchanger adapted to carry a fluid through or alongside the reaction volume, allowing the transfer of heat energy from the reaction volume to the fluid, thus reducing the temperature in the reaction volume. Alternative or additional cooling means would be apparent to the person skilled in the art, such as electrical cooling means.

Preferably the heat exchanger of the electrolysis apparatus and the hydrogenation apparatus are in fluid communication such that at least a portion of the heat from the hydrogenation apparatus can be used to heat the electrolysis reaction. Such an arrangement allows for the use of heat energy, thus improving efficiency. However, it may be that in certain circumstances the amount of heat energy being produced in the hydrogenation reaction may be too much or little to provide the desired corresponding heating of the electrolysis reaction, and thus additional heating or cooling means may be included to compensate for any such imbalance.

In a preferred embodiment the input water for the electrolysis apparatus can be used to directly cool the hydrogenation apparatus reaction volume. For example, the input water can flow around conduits in which the hydrogenation reaction occurs, e.g. the tubes defining the hydrogenation reaction volume. Preferably this can be achieved using the combined Sabatier/electrolysis apparatus described below.

Preferably temperature control means are provided which allow the temperature of the electrolysis apparatus and/or the hydrogenation apparatus to be retained at the desired temperatures. Preferred temperatures are set out above. Such means may include one or more valves to control the rate of flow of fluid within the heat exchangers present in the electrolysis apparatus and/or hydrogenation apparatus. There may be more than one heating and/or cooling systems present in the apparatus. It is preferred that of the heat produced in the apparatus can be used to heat other parts of the apparatus, e.g. the exothermic hydrogenation of $CO_2$ can be used to heat the feedstock for electrolysis. However, additional heating or cooling means may be provided to deal with any imbalances of heat and/or to assist with start-up of the apparatus.

In some preferred embodiments the system comprises electricity generation means configured to use residual heat present in the oxygen and/or hydrogen (optionally after it has been used to heat the input water) to generate electricity. Such electricity can advantageously be used to drive electrolysis. Suitably the electricity generation means comprises one or more boilers adapted to generate steam, using heat in said oxygen and/or hydrogen, which is then used to drive one or more steam turbines and thereby generate electricity. This provides a mechanism by which heat energy, which might otherwise have been lost to the atmosphere, can be used to drive electrolysis.

In preferred embodiments steam bridges are provided which allow steam generated from the boilers to bypass the LP turbine and condenser and be returned as input water for electrolysis. This is particularly useful where it is desirable to retain the maximum amount of heat in the system, e.g. during start up. This allows the system to avoid energy loss, e.g. in condensers after the steam turbine, when it is desirable to retain heat in the system. The steam bridges suitably comprise valves which are operable to divert steam from the high pressure side of the LP turbine into a pipe leading to the input conduit thus providing elevated temperature input water for electrolysis, rather than allow it to pass through the LP turbine and condenser.

Suitably the electrolysis apparatus comprises a solid oxide electrolyser. As discussed above, the use of yttria-stabilised zirconia is preferred.

The hydrogenation apparatus comprises a metal catalyst, preferably Ru on $Al_2O_3$, although other catalysts may be suitable. The catalyst will typically be mounted on a suitable substrate. Preferably the catalyst is mounted on a reusable substrate which is adapted to be removed from the reaction volume, e.g. to be replaced.

In a further aspect, the present invention provides a method for generating electricity from an energy source, said method comprising the steps of:
a) providing an electrical energy source;
b) using electrical energy from said source to electrolyse water to form hydrogen and oxygen;
c) using hydrogen thereby formed to hydrogenate carbon dioxide to form a hydrocarbon fuel in the form of methane;
d) optionally converting a least a portion of said methane to form a secondary fuel;
e) providing the fuel product of step c) or d) to a secondary electricity generator capable of deriving electrical energy from said fuel product; and
f) producing electrical energy.

In a preferred embodiment the electrical energy is provided by operating a non-fossil fuel energy generator to obtain electrical energy, more preferably a renewable energy generator. In an alternative embodiment the electrical energy source is an electrical grid, e.g. during periods of overproduction, low demand, and/or low cost.

Preferably the method involves providing oxygen to said secondary generator for oxidation of the fuel. More preferably at least a portion of said oxygen is produced from the hydrolysis of water (typically oxygen which is co-produced with the hydrogen in step b).

Preferably oxidation (e.g. combustion) of the fuel is conducted in the presence of substantially pure oxygen, i.e. 90% by volume or higher, 95% by volume or higher oxygen, more preferably 99% by volume or higher. This is known in the art as 'oxy-fuel combustion'. The use of substantially pure oxygen in the oxidation of a hydrocarbon is advantageous as the output products, assuming complete oxidation of the fuel, are simply water and carbon dioxide, assuming appropriate conditions are used. In contrast to the situation when air is used, there are no undesirable products such as nitrous oxides. Thus a significant advantage in using oxy-fuel combustion is that, after condensing out the water vapour, the resulting flue gas will be very pure (>95%) in $CO_2$, and will be without the nitrous oxides and sulphur dioxide resulting from combustion of impure coal or natural gas in air. This greatly facilitates carbon dioxide capture as there is no need to separate carbon dioxide from remaining air gases such as nitrogen and other gaseous components. Separation of carbon dioxide from air is difficult to achieve and represents a massive efficiency loss for conventional carbon capture techniques.

Thus the present invention provides the enormous benefit that it provides both the fuel and the oxygen for oxy-fuel combustion. This in turn greatly facilitates the subsequent capture of the carbon dioxide produced.

Another advantage of the present invention is it allows the production and subsequent oxidation of a substantially sulphur free fuel, which has advantages in avoiding pollution and avoiding "poisoning" of catalysts, electrolytes etc., and/or costs of sulphur removal.

The method of the present invention may preferably comprise capturing carbon dioxide produced as a result of the generation of electricity. This carbon dioxide can conveniently then be used as a feedstock for the hydrogenation reaction of step c). In such an embodiment there is the significant advantage that electricity generation becomes 'carbon neutral'.

It is preferred that the secondary generator comprises a combined cycle gas turbine (CCGT). It is further preferred that the CCGT is adapted for oxy-fuel combustion, which thereby provides the advantages discussed above. Alternatively, the secondary generator may comprise a fuel cell or a hybrid fuel cell.

In certain embodiments it is preferred that the secondary generator is a combined heat and power (CHP) system, also known as a District Heating system. Such systems provide additional efficiency benefits. The present invention provides a source of fuel that is potentially extremely clean and thus well adapted to generation close to areas where heating is required.

In some embodiments the method will comprise transporting at least the fuel from the location at which it is produced (typically at or near a renewable energy source) to the secondary generator. This may be achieved using a transportation vehicle such as a ship, train or lorry, or may be achieved using a pipe. Preferably oxygen is also transported from the location of its production to the secondary generator.

It is a significant advantage of certain embodiments of the present invention that it allows the use of renewable energy sites, which are typically distant from population centres, to produce a fuel which can be transported by conventional means for use in electricity generation at or near such population centres. As such, the massive losses associated with directly transporting electricity across such distances can be avoided, as can the costs, environmental and aesthetic issues associated with cables and pylons.

It is another significant advantage of certain embodiments of the present invention that they allows 'surplus' electricity from the grid to be converted to chemical energy, which can then be reconverted to electricity when it is desirable to do so, e.g. at times of high demand. This has advantages in terms of allowing the demand on non-flexible electricity generation systems to be smoothed out, and also accommodating difficulties in the predictability/controllability of electricity from non-fossil fuels. For example, generation capacity provided by wind, wave or tidal power outside of times of demand, which might otherwise not have been useful, can be stored as chemical energy for future use at times of peak demand. Thus, in some ways the present invention provides a novel and scalable equivalent to known pumped storage technology. This provides a long needed solution to the problem of variable and uncontrollable generation capacity from green energy sources.

A further advantage of the present invention is that it can provide a source of water at the site of generation, which can be used as drinking water or for other purposes, such as providing a source of water for use in steam generator systems, e.g. to make up any water loses in a Rankine cycle generator system.

In a further aspect the present invention provides a system for generation of electricity, said system comprising:
a) an electrical energy source;
b) an electrolysis apparatus electrically coupled to said electrical energy source operable to electrolyse water to form hydrogen and oxygen;
c) gas handling means to collect oxygen and hydrogen produced in said electrolysis apparatus;
d) a source of carbon dioxide;
e) a hydrogenation apparatus adapted to hydrogenate carbon dioxide to form methane using said hydrogen; and
f) a secondary electricity generator capable of deriving electrical energy from said methane or a derivative thereof.

As discussed above, the electrical energy source can be a non-fossil fuel generator operable to obtain electrical energy from a non-fossil fuel energy source (e.g. a renewable generator), or it can be a connection to an electricity grid.

The system may further comprise transportation means to transport methane (or a derivative thereof such as methane hydrate), and preferably also oxygen from the location of production of the gases to the secondary electricity generator. This is particularly preferable when the secondary generator and the hydrogenation apparatus are spatially separated. The transportation means may comprise a tanker in the form of a ship, railway stock or lorry, or it may be a pipeline. Pipelines and ships for the transport of methane (natural gas) are well known, and are used extensively for the transport of natural gas in conventional fossil-fuel extraction technologies. They could be readily applied to the present invention.

Preferred secondary generators are discussed above, as are details of other components of the system, and thus they will not be discussed again with reference to this aspect of the invention.

In a further aspect, the present invention provides a pipeline for the transport of two fluids comprising a first pipe adapted for carrying a first fluid within the first volume defined by the lumen thereof, and a second pipe surrounding said first pipe, wherein the second fluid can be carried within a second volume defined by the outer surface of the first pipe and the inner surface of the second pipe.

Accordingly, the lumen of the first pipe provides a first flowpath for a first fluid. The first volume defined by the interior of the second pipe and the exterior of the first pipe form a second flowpath for a second fluid.

Preferably the first and second pipes have a substantially circular cross-section.

Preferably the first and second pipes are axially parallel. More preferably the first and second pipes are coaxial, and optionally concentric.

Preferably the pipeline as adapted to carry a reactive fluid (such as oxygen, hydrogen or methane) in the lumen of the first pipe, and an inert fluid (such as carbon dioxide or nitrogen) within the volume defined by the outer surface of the first pipe and the inner surface of the second pipe.

In a highly preferred embodiment the total cross-sectional area of the pipeline is divided such that of the lumen of the first pipe has a cross-sectional area of approximately ⅔ of the total area, and the second volume has a cross-sectional area of approximately ⅓ of the total area. In such an embodiment the volumes are adapted to carrying fluids in the amounts corresponding to the stoichiometric ratios of carbon dioxide and oxygen as used in other aspects of the present invention.

The pipeline will typically comprise suitable valve gear and fittings to control and manage flow of the fluids within the pipeline.

The fluids may be gases or liquids.

In further embodiments the pipeline may be adapted to carry more than two fluids, for example three or more gases. For carrying three fluids the pipeline may comprise a third pipe surrounding the second pipe, thus providing an additional volume for the transport of a fluid, the volume defined by the inner surface of the third pipe and the outer surface of the second pipe. It will be appreciated that further pipes could be added as required to provide additional volumes, in the manner of additional 'layers' of pipes.

A particularly preferred embodiment is adapted to carry four fluids. It comprises a first pipe defining an inner lumen, a second pipe, a third pipe, and a fourth pipe arranged coaxially and concentrically, thus defining four flowpaths for fluids. In a preferred embodiment the pipeline is adapted to carry a reactive fluid within the first pipe, an inert fluid in the second volume, a reactive fluid in the third volume, and an inert fluid in the fourth volume. In a preferred embodiment the pipeline is adapted to carry methane or another hydrocarbon or hydrocarbon derivative within the first pipe, carbon dioxide in the second volume, oxygen in the third volume, and carbon dioxide in the fourth volume. In such an embodiment the reactive fluids are each separated from each other to some extent by an inert fluid.

Such a general arrangement, i.e. each reactive fluid being jacketed by an inert fluid could be further extended by providing further 'layers' via additional pipes.

In a further aspect the present invention provides a combined method of generating methane and performing electrolysis comprising:

carrying out a high temperature electrolysis process to form oxygen and hydrogen from input water (e.g. in the form of steam);

carrying out the hydrogenation of carbon dioxide using the hydrogen thereby produced; and using heat produced in the hydrogenation reaction to heat input water for use in the electrolysis process.

Preferably the method involves bringing the input water for use in the electrolysis process into thermal communication with the hydrogenation reaction, such that the input water is heated and the hydrogenation reaction is cooled.

Preferably the method comprises using at least a portion of the oxygen and/or hydrogen produced in the electrolysis process to heat the input water for use in the electrolysis process. This allows at least some of the heat energy contained in the products of electrolysis to be used to heat the input water, thus raising overall efficiency of the process.

In a preferred embodiment at least a portion of the oxygen and/or hydrogen generated in the electrolysis process is used to drive electricity generation means. The oxygen and hydrogen are at high temperatures, and thus can suitably be used to generate steam in a boiler (e.g. in a Rankine cycle boiler) and thereby drive an electricity generator (e.g. a steam turbine). This can optionally be used in combination with the above mentioned process of using the hydrogen and/or oxygen to heat the input water. This allows heat energy which might otherwise have been lost from the system to be used to generate electricity. This electricity is preferably used to electrolyse water.

In a further aspect the present invention provides a combined electrolysis/hydrogenation apparatus for use in the generation of methane and performing electrolysis comprising:

a high temperature electrolysis apparatus adapted for electrical coupling to an electrical energy source, said high temperature electrolysis apparatus being operable to electrolyse water at high temperature in an electrolysis chamber using electrical energy to form hydrogen and oxygen, the high temperature electrolysis apparatus comprising a water feed conduit adapted to carry water (typically in the form of steam) to the site of electrolysis;

gas handling means to collect oxygen and hydrogen produced in said electrolysis apparatus comprising gas-carrying conduits adapted to carry the oxygen and hydrogen;

a hydrogenation apparatus adapted to hydrogenate carbon dioxide to form methane using said hydrogen produced in the high temperature electrolysis apparatus comprising a hydrogenation chamber in which hydrogenation of carbon dioxide occurs; and wherein at least a portion of the hydrogenation chamber is in thermal communication with the feed conduit, such that heat generated in the hydrogenation reaction can heat water to be electrolysed.

As discussed above, in preferred embodiments a non-fossil fuel energy generator is used to produce electrical energy to drive electrolysis. Alternatively electricity from an existing electrical grid can be used.

In one embodiment the hydrogenation chamber is in thermal communication with the feed conduit. Preferably the hydrogenation chamber comprises a plurality of conduits (e.g. tubes) which pass through the lumen of the feed conduit such that at least a portion, preferably substantially all, of the conduits is in contact with water therein. Thus the conduits/tubes act as heat exchangers to heat the water for electrolysis and cool the hydrogenation reaction. The conduits (tubes) may be adapted to maximise the transfer of heat, e.g. they may include means to increase the surface area of the conduits such as fins or coils, or the tubes may be profiled to increase their surface area. Other suitable means to maximise heat transfer will be apparent to the person skilled in the art.

Preferably at least a portion of the oxygen and/or hydrogen gas-carrying conduits is adapted such that they are in thermal communication with the feed conduit. For example, the gas carrying conduits can comprise a heat exchanger which is in thermal communication with the feed conduit. Preferably both of the oxygen and hydrogen gas-carrying conduits comprise a portion which is in thermal communication with the feed conduit. In a preferred embodiment the oxygen and hydrogen gas-carrying conduits comprise a plurality of tubes which pass through the lumen of the feed conduit such that they are in contact with water therein. The tubes can be adapted to maximise heat transfer, as mentioned above. Thus the hot gases produced during electrolysis can be used to heat the feed water, thus providing a convenient way of heating the water and avoiding energy waste.

It is preferred that the combined electrolysis/hydrogenation apparatus is adapted such that heat transfer from the hydrogenation reaction to water in the feed conduit occurs upstream from heat transfer from the gas-carrying conduits. This is because the gas carrying conduits are typically at a higher temperature than the hydrogenation chamber, and thus the present arrangement allows for more efficient heating of water in the feed conduit.

In a preferred embodiment the gas carrying conduits pass through a heat exchange apparatus, e.g. a boiler such as a Rankine cycle boiler, which is adapted to generate steam which can be used to drive a steam turbine to generate electricity. Preferably the gas carrying conduits pass through the heat exchange apparatus downstream from when they pass in thermal communication with the feed conduit, i.e. after heat has been transferred to the feed conduit. This arrangement allows even more of the heat in the hydrogen/oxygen to be reused, in this case to generate electricity. Suitably the electricity generated is used in electrolysis. Optionally the hydrogen and oxygen carrying conduits can pass through separate heat exchange apparatuses, or they may pass through the same heat exchange apparatus, provided of course that the streams of hydrogen and oxygen are kept separate. Where separate heat exchange apparatuses are provided, they can feed steam into a single steam turbine, or more than one steam turbine.

In a preferred embodiment of the present invention there is provided a separator to separate water which exits the electrolysis apparatus from the hydrogen/oxygen and return it to the feed conduit. This provides a source of already hot water to the feed conduit, which further allows for heating of the input water.

Suitably the combined electrolysis/hydrogenation apparatus comprises one or more auxiliary heaters to heat the apparatus during a start-up phase, and optionally during further operations, should this be required. Suitably a heater is adapted to heat water in the feed conduit. Alternatively or additionally the apparatus comprises a heater to directly heat the electrolysis chamber. Suitably the one or more heaters are electrical heaters. Suitable heaters are well known in the art.

In a further aspect the present invention provides a method of electrolysis and generation of methane comprising the steps of:
  hydrogenating carbon dioxide to form methane;
  using heat produced in the hydrogenation reaction to heat input water prior to electrolysis; and
  performing high temperature electrolysis on said input water to form hydrogen and oxygen.

Accordingly, heat produced by the exothermic hydrogenation reaction is used to heat the input water for the electrolysis reaction. This reduces the need for additional heating of the input water to get it up to the desired temperature for high temperature electrolysis. It also allows for cooling of the hydrogenation reaction (e.g. the Sabatier reaction) without the heat energy being wasted. However, additional heating and/or cooling can be applied if required.

Preferably the method comprises using the hot hydrogen and/or oxygen that is produced in the electrolysis process to heat the input water prior to electrolysis. In this embodiment, the hot products of the electrolysis reaction can be used to further heat the feed water. This allows the heat energy in the products to be used to bring the feed water up to a high temperature, thus reducing or avoiding the need for additional heating.

The method may further comprise using the hot oxygen and/or hydrogen to drive electricity generation, e.g. through a Rankine cycle boiler connected to a generator. This allows for additional energy in the oxygen and/or hydrogen to be reclaimed. Suitably the electricity thereby produced is used to electrolyse water.

Suitable apparatus to perform this method is set out above, and the method may be adapted to best utilise the features of said apparatus.

DESCRIPTION OF EMBODIMENTS OF THE INVENTION

Embodiments of the present invention will now be described, by way of example only, with reference to the accompanying drawings in which:

FIG. 1a shows a schematic diagram of energy transfer according to the present invention and FIG. 1b shows a particular embodiment of the invention in which time-phased energy transfer is conducted.

FIG. 2 shows a flow chart of one embodiment of the present invention.

FIG. 4a shows a schematic representation of inputs, take-offs and storage capabilities associated with the present invention.

FIG. 4b shows a pipe system according to the present invention for transporting products of the present invention.

FIG. 5 shows a schematic representation of a combined cycle oxy-fuel gas turbine generator with $CO_2$ recovery.

FIG. 6 shows a combined 2-stage fuel and oxygen production process.

FIG. 8 shows a scheme for the conversion of methane into other useful products, e.g. petrochemical feedstocks.

FIG. 9 shows an embodiment of time-phased energy transfer from the electricity grid by night (or other time of low demand) into electricity supply and district heating.

GENERAL DISCUSSION OF THE PRESENT INVENTION

Figure 3A:
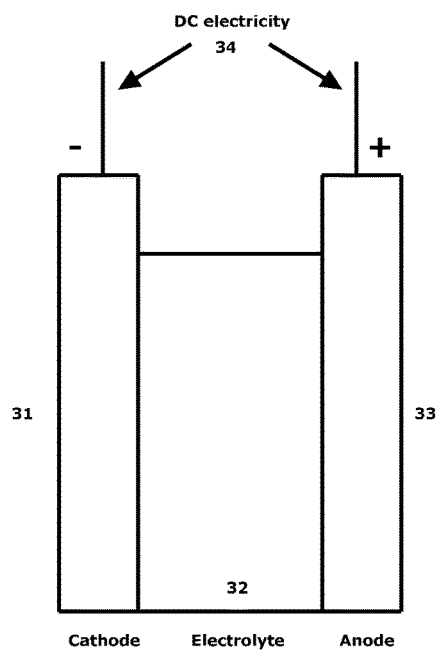
FIG. 3a shows a schematic representation of an electrolysis chamber.

Detailed below are various aspects which can be combined to provide a fully-integrated approach to energy storage and generation, preferably without the emission of $CO_2$ to the atmosphere. This is achieved via the production and subsequent combustion of a hydrocarbon gas as an energy storage medium (which will be referred to at times as a 'thermogas'), by combining the emerging technologies of oxy-fuel combustion, catalytic conversion of $CO_2$ into methane, and increasingly efficient electrolysis of water into hydrogen and oxygen. It is believed that the approach outlined here represents a method of greatly increasing the usefulness of alternative energy generation and, if implemented on a large scale, has the potential to greatly reduce our dependence on fossil fuels. It also represents a method of storing energy produced at off-peak times for use when demand is high.

Making fuels from various alternative energy sources has been postulated and studied at length for many years in terms such as "the hydrogen economy", "the methane economy" and "the methanol economy". The present invention is based on the concept that an energy economy can be based upon a chosen combustible gas or hydrocarbon fuel derived from alternative energies. Furthermore, the present invention extends the concept to integrate it with an energy transfer process. Means will be described to recover $CO_2$ from electricity production which will then be used to maintain the energy transfer in a recurrent process.

Electricity cannot be readily stored, but combustible fuel and oxygen can, albeit in liquid or solid form. The present invention could deploy vast storage capabilities for fuel and oxygen at strategic locations. Current technology allows for upwards of 200,000 $m^3$ storage per tank or ship tanker. These storage capabilities can be compared against the commodities required for a 1,000 MW(E) oxy-fuel CCGTEG operating at full load for 12 hours per day for 3 months: approximately 400,000 $m^3$ of liquid oxygen and 275,000 $m^3$ of fuel (if liquid methane), whilst approximately 200,000 $m^3$ of $CO_2$ stored as a solid would be produced in that time.

Such stored energy being readily available to meet electricity demand, where and when required, has several benefits compared to the current practice of electricity generation. For example where wind energy is used to generate electricity to the grid, it cannot be relied upon to meet the demand at any particular time. In contrast the present invention would use renewables such as wind, wave, tide or solar energy to make fuel and oxygen, e.g. for transfer and storage local to the point of use, subsequently meeting electricity demand when it is required.

The current practice is to extend the electricity grid system to interconnect electricity producing energy sources with places of electricity demand. Sometimes this is not possible or prohibitively expensive. For example the geothermal energy of Iceland cannot help to meet electricity demand in America, there being no electricity grid connection between source and demand. The present invention provides ways of securing, storing, transporting and delivering energy from distant alternative sources to electricity demand locations. However, the invention can also be deployed local to the demand using the electricity grid for renewable energy transfer. An example would be overnight production and energy storage followed by electricity supply during days and evenings.

At present District Heating (or Combined Heat and Power) using otherwise wasted heat from electricity generating stations is practiced where possible because it provides means to raise the thermal efficiency of fuel utilisation. However the pollution associated with current fossil power plants all but prohibits their use in urban areas. The present invention can be more acceptable within the urban setting as emissions are virtually zero, and thus District Heating could be more widely practiced achieving further savings in $CO_2$ emissions.

Water is a precious commodity in certain parts of the world. Desalination methods of water production and supply are widely in use, often by fossil fuel combustion involving $CO_2$ emissions. The present invention describes how water is produced during the electricity generating process which could then, after conditioning, be made available in various forms as a useful product. The water could be still or carbonated for drinking or demineralised for industrial or other use. Some 3 million liters or so could be produced from a 1,000 MW oxy-fuel CCGTEG running at full load for 24 hours.

The transportation of liquid natural gas and other cryogenic commodities by ship tankers is widely practiced. The present invention could involve such methods as one of the means of transportation of the commodities involved. Another means of transportation could use existing pipeline technology as in the Eurasian pipeline network. Gas transference through the pipelines is by means of pressure boosting plants which typically take in gas at greater than 2 bars and pressurise at up to 10 bars to force the gas to the next booster point or terminal. The present invention could use similar methods except three commodities would typically be involved: fuel, oxygen and $CO_2$. Moreover one aspect of the invention shows how existing pipelines could be utilised for transference of the three commodities.

FIG. 1*a* illustrates how energy from renewables 11 can be transferred into electricity and District Heating 12 for supply to consumers.

Means will be shown how water ($H_2O$) 16 and carbon dioxide ($CO_2$) 15 can be made into oxygen ($O_2$) 14 and a combustible fuel, preferably methane ($CH_4$) 13, by DC electricity 11 derived from renewable energies. The $O_2$ 14 and $CH_4$ 13 are transferred to a heat engine electricity generator 19 to supply electricity to the grid or for local use 12. The heat engine exhaust containing $CO_2$ and $H_2O$ is cooled to enable separation and compression of the $CO_2$ for transfer back to the fuel/oxygen production site 18 to continue the process. Hence energy transfer from renewable energy sources into electricity for supply to the grid is made possible with no emissions to atmosphere. The District Heating 12 is optional, but preferable.

In addition to energy, effectively water is transferred from the production site 18 to the supply site 19. Water usage 16 is necessary at the production site 18 but water 17 is made as a product of combustion at the supply site 19.

FIG. 1b shows time-phased energy transference, an embodiment of the present invention, which can optimally be located at a single site. 'Time-phased' is used herein to describe a method or system which allows electrical energy produced at a certain time to be stored (as chemical energy) for release as electrical energy at another time. This is essentially the effect achieved by existing techniques such as pumped storage, but existing technologies are limited by the size of the storage facilities and the cost of infrastructure. The present invention provides a far more flexible, scalable and convenient solution to this problem.

At periods of low demand or over-production (e.g. at night or where renewable production is at high levels due to high winds or the like), electricity is taken from the grid 110 through rectifiers 130 to supply DC electricity to methane and oxygen production plant 128, which will be described in more detail below. $CO_2$ 115 and water 121 taken from the storage tanks 124 and 127 are used in plant 128 to produce methane 117 and oxygen 119 for collection in storage tanks 125 and 126. Make up water 123 would be made available as required to water 121. At periods of high demand (e.g. during the day or when renewable production is low) methane 118 and oxygen 120 would be taken from said storage tanks 125 and 126 and transferred to a heat engine electricity generator 129 (e.g. a CCGT plant or fuel cell) to supply electricity 112 to the grid 110 and heat to district heating 114. The heat engine exhaust is cooled to enable separation and compression of the $CO_2$ 116 into storage tank 124. The water 122, after being degassed of $CO_2$ would be collected in storage tank 127. Hence energy taken from the grid by night is used to supply emissions free electricity to the grid by day. The benefits of such a system are clear; allowing somewhat sporadic energy generation from renewables to be captured efficiently for use when demand is high, and allowing general electricity production to be smoothed out.

District heating energy can also be provided by night 113 or by day 114. FIG. 9 shows a system for time-phased energy transference in more detail.

The means to achieve the energy transfer referred to above is explained in concept by FIG. 2 where, in the case illustrated, methane is the preferred fuel. Further steps in the flowchart would be necessary for other fuels. Existing technology can enable methane feedstock to be used to produce fuels with higher heat content for the energy transference process but methane is initially preferred because of its compatibility with existing natural gas pipelines and utilities.

1. DC electricity is generated by alternative non $CO_2$ emitting methods or taken from the grid and used to power electrolysis of $H_2O$ (from local sources), typically on a large scale (21);
2. $CO_2$ and $H_2$ are reacted over a metal catalyst to form the preferred combustible fuel $CH_4$ and $H_2O$ (22);
3. The $H_2O$ produced is preferably recycled into the electrolysis (step 1), while the $CH_4$ and $O_2$ are recovered (23);
4. The $CH_4$ and $O_2$ are transported to a heat engine electricity generating plant, preferably an oxy-fuel combined cycle gas turbine electricity generator (CCGTEG) of a standardised design (24);
5. Electricity is generated to meet demand by the combustion of the $CH_4$ in the $O_2$ (oxy-fuel combustion process) (25);
6. Part of the water produced by the combustion is used as make-up to the Rankine steam cycle; the remaining water can be used as a product as carbonated or still drinking water or as demineralised water (26).
7. The $CO_2$ produced by the combustion is recovered and transported back for use in the hydrogenation process (step 2) to enable recurrent energy transfer (27).

These steps can be viewed as belonging to one of three sections: the 'upstream' processes (stages 1, 2 and 3); the 'downstream' processes (stages 5 and 6); and transportation of materials (stages 4 and 7). The present invention encompasses the entire system as well as certain individual parts of it.

The core aspects of the various aspects of the present invention are described in detail in the text and in FIGS. 3 to 9 below.

Electrolysis of Water

To obtain the $H_2$ necessary for the production of methane via the Sabatier process, it is envisaged that large-scale electrolysis of water will be carried out. The basic reaction is given by the equation:

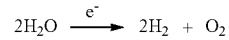

$$2H_2O \xrightarrow{e^-} 2H_2 + O_2$$

Much research has been focused on a means to improve the efficiency of this reaction, as could be expected for such a simple potential route to the valuable commodities hydrogen and oxygen. Recent progress in the development of solid oxide electrolyser systems[7] has raised strong possibilities for increased efficiency. In particular, the use of yttria-stabilised zirconia ('YSZ', $Y_2O_3$ in $ZrO_2$), a gastight electrolyte which conducts $O^{2-}$ ions well at high temperatures, greatly simplifies separation of the hydrogen and oxygen products. Furthermore, it has also been demonstrated that a sizeable improvement in the efficiency of the electrolysis reaction can be obtained if a high operating temperature can be maintained[8]. Accordingly, it is advantageous that the exothermic Sabatier reaction could be used to supply substantial amounts of heat to the electrolysis cells; for example, by the use of pressurised steam as a medium for heat transfer from the Sabatier reactors, the heated steam then fed (along with that directly produced by the Sabatier reaction) into the electrolysis cells for conversion to $H_2$ and $O_2$. In this way, the efficiency of the $H_2$ generation could be further increased. The hydrogen produced would then be fed back to the Sabatier reactors, giving a continuous two-step process that uses $CO_2$ and $H_2O$ to produce $CH_4$ and $O_2$, summarised by the equation:

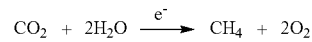

$$CO_2 + 2H_2O \xrightarrow{e^-} CH_4 + 2O_2$$

The $CH_4$ and $O_2$ will then be used in the 'downstream' plant (e.g. electricity generation by combustion-fired CCGT) as described below.

FIG. 3a shows a schematic diagram of a basic electrolysis cell. A DC electric potential 34 is applied between the cathode 31 and anode 33, imparting to them net negative and positive charge respectively. Electrons are conducted through the electrolyte solution 32. At the cathode, which is rich in electrons, $H^+$ ions combine to form $H_2$, while at the electron-deficient anode, $O^{2-}$ ions give up electrons and form $O_2$. These gases are in a different state from the electrolyte 32, and are thus easily drawn off as products.

Generation of Methane

Figure 3B:
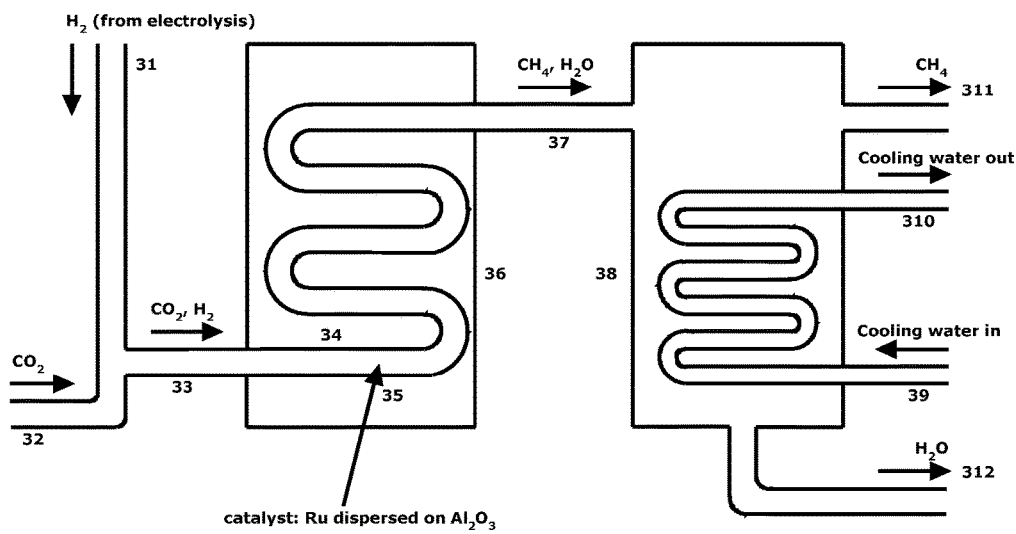
FIG. 3b shows a schematic representation of an apparatus for the hydrogenation of carbon dioxide.

FIG. 3b shows a potential layout of methanation plant for use in conjunction with large-scale electrolysis. $H_2$ from the electrolysis plant enters through pipe 31 and joins a stream of $CO_2$ from pipe 32. It is envisaged that the $CO_2$ entering through pipe 32 will be obtained from the oxy-fuel CCGTEG plant as previously described. The combined stream then passes through pipe 33 into the methanation reactor tube 34, where it reacts across metal catalyst 35 to form $CH_4$ and $H_2O$.

The methanation is currently envisaged to take place via the Sabatier process. The reaction of carbon dioxide ($CO_2$) and hydrogen ($H_2$) in the presence of a metal catalyst to form methane ($CH_4$) and water ($H_2O$) was first demonstrated by Paul Sabatier in the early $20^{th}$ Century.[4] Recent efforts to improve the efficiency and commercial viability of the process have been largely driven by its potential applicability in NASA's space program[5,6], but to the present inventor it is also an ideal means of generating a fundamental thermogas ($CH_4$) and in the process using $CO_2$, precisely the gas which we wish to avoid emitting to the atmosphere;

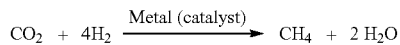

with the metal catalyst 35 ideally being the best available using leading-edge technology, currently Ru dispersed on $Al_2O_3$.

This reaction has been shown to be exothermic, with optimum product yield obtained around 300° C. (As the temperature increases above this point, the back reaction becomes important, reducing yield.) Much research continues to be devoted to optimisation of both the metal catalyst and the reaction conditions. Recently, macroporous Ru-on-$Al_2O_3$ catalysts have shown to give good selectivity and large surface areas for reaction within a small reactor volume[5], a promising development which could facilitate the implementation of the Sabatier process within our method. With so many molecules reacting in a small reactor vessel, the issue of heat transfer from the reactor becomes paramount, since if the temperature begins to increase above 300° C., efficiency is lost as described above. Accordingly, long, thin cylindrical reactor 'tubes' have been proposed[6]. Our proposal intends that the large quantities of heat given out by the Sabatier reactors will be utilised to provide a benefit to another step of the method, as will be described below.

As touched on above, the Sabatier reaction is a highly exothermic process, and suffers from undesirable efficiency loss at temperatures significantly above 300° C. Consequently, the reaction vessel should take the form of the long, narrow reactor tubes 34. Furthermore, these are encased within a pressure vessel 36, in order to maintain them at the optimal reaction temperature of 300° C. or thereabout. The optimum temperature for the Sabatier reaction, in the context of efficiency of the entire system, can be determined through operational trials.

The product stream of $CH_4$ and $H_2O$ from methanation reactor tube 34 passes through pipe 37 and into condenser 38 in order to separate the $CH_4$ and $H_2O$. A stream of external cooling water is passed through the condenser in circuit 39, withdrawing heat from the product mixture and resulting in condensation of the steam. The $CH_4$ remains in the gas phase and passes out of the condenser through pipe 311. The resulting liquid water is taken off from the bottom of the condenser through pipe 310. In one configuration, this water could be used, possibly along with a top-up supply, as a heat transfer fluid to be passed through vessel 36.

Transportation of Materials

The need to continuously move large quantities of $CH_4$ and $O_2$ from upstream to downstream plant, and the parallel return of $CO_2$ to the upstream, may necessitate the development of large-scale material transportation infrastructure. There are, at present, two principal means for the movement of large quantities of potentially-hazardous fuel: gas pipeline and ship tanker containing liquefied materials, both of which are presently employed on a global scale by the fossil fuel industry. Our investigations indicate that a hybrid approach, combining both methods of transportation, would be the most effective route to address this issue.

The large liquefied natural gas (LNG) tankers currently in operation have a capacity of approximately 250,000 m³, capable of transporting over 120,000 tonnes of liquefied $CH_4$ in one shipping[18]. This would be sufficient to fuel a 1 GW CCGT (of 60% efficiency), running 12 hours a day, for over three months. Alternatively, two full tankers of this capacity, running once a fortnight back and forward from the upstream to downstream plants, would be capable of carrying enough liquid methane to provide electricity for the whole of Scotland by combustion in CCGT plants. It would therefore appear that the ship tanker approach holds excellent potential for the transport of the chosen thermogas (e.g. methane), although this could also be done by gas pipeline, as illustrated below.

The transport of the $O_2$ and $CO_2$ also needs to be addressed. Both could theoretically be done by ship tanker: the $CO_2$ frozen and carried at low temperature in the form of dry ice ($CO_2(s)$), and the oxygen liquefied and transported in an analogous method to the methane. However, a potentially more elegant solution lies in the use of a pipeline network. Here, the idea is to use four-layer pipeline, as shown in FIG. 4b.

FIG. 4b shows one possible configuration of transference means consisting of a composite pipeline system, transporting oxygen and methane to the CCGTEG plant and returning $CO_2$ to the fuel production location. Methane is transported through the innermost pipe 41. The $CO_2$ is divided into two parts, to protect and separate the fuel and the oxygen. One part is passed through pipe 42 to further isolate the methane from the oxygen in pipe 43, the other part being transported through the outermost pipe 44, protecting the oxygen from the outside environment. End connections 45 and 46 facilitate the take-off of the methane and oxygen respectively. The $CO_2$ is passed into the pipeline through connection 47, with part passing into pipe 42 and part into pipe 44 as described above.

Static and differential pressure sensors between $O_2$ and $CO_2$ (48) and between $CH_4$ and $CO_2$ (49) monitor the absolute and relative pressures of each gas at all times, providing monitoring and control in order to ensure safe and effective pipeline operation.

Figure 7:
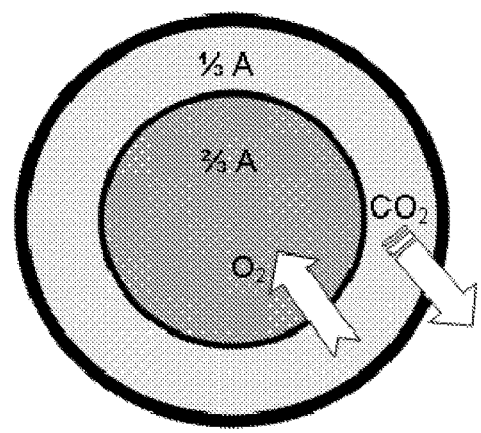
FIG. 7 shows an alternative pipe according to the present invention for use in transporting products.

FIG. 7 shows a cross-section of an alternative, two-layer pipeline, adapted to carry oxygen and carbon dioxide. The $O_2$ is injected to the pipeline at the upstream plant, and is pumped in the downstream direction through the inner pipe. Likewise, the $CO_2$ is pumped back to the upstream from the CCGT plant through the outer pipe, as indicated. Twice as much total cross-sectional area of pipe is required for the $O_2$ compared with the $CO_2$, due to the stoichiometry of the combustion reaction. In the case of a longer pipeline, compressor stations would be situated along the route, with entirely separate circuits to ensure no mixing of the gases. This arrangement has the advantage of the pipe containing the high fire-risk gas ($O_2$) effectively being contained within a blanket of $CO_2$, further isolating it from the outer environment and thus providing a very useful safety buffer. Each pipeline would be constructed of carefully-selected materials and monitored rigorously to ensure safety.

The rate at which the oxygen is allowed to travel through a pipeline is regulated, with its maximum velocity controlled by the 'impingement velocity curve' (IVC) for the specific pipeline material in use.[19]. This identifies an inverse relationship between pressure and maximum velocity: for example, for a steel pipe, $O_2$ at 0.6 MPa has a maximum allowed velocity of 7.5 ms$^{-1}$. The IVC thus implies a maximum transfer rate which depends on the pipeline diameter (and thus the cross-sectional area), multiplied by a constant (P.V, as these are inversely proportional for the curve region in question). In order to fuel a 1 GW CCGT plant of 60% efficiency, a cross-sectional area of 2.09 m$^2$ is required for oxygen being piped at the limiting conditions of the IVC. This corresponds to an $O_2$ pipe of internal diameter 1.64 m. This would be surrounded by an outer $CO_2$ pipeline, which requires a total available cross-sectional area (excluding the $O_2$ inner pipe) of 1.05 m$^2$, leading to a total pipeline diameter of 2.04 m.

Generation of Electricity from Thermogas

The large quantities of thermogas and oxygen produced will be transported and/or stored for use to meet electricity demand in a downstream generating plant.

Fossil fuel electricity generating stations are currently multifarious in their design in order to cater for the variety of available fuels. The present invention will provide means to have a single basic design of generating stations to meet electricity demand that need only vary with regard to size.

Power generation is envisaged to be carried out in a combined cycle gas turbine (CCGT), currently in widespread use in natural gas-fired power plants worldwide,[13, 14] but crucially, adapted for oxy-fuel combustion, as described below.

The principle of generation by CCGT is well-understood, and CCGTs are in common use throughout the world. The design combines a primary-loop gas turbine cycle, operating at very high temperature, with a secondary-loop steam turbine cycle which draws its heat from the still-high-T outlet of the gas turbine. In the gas turbine cycle, a working fluid is compressed and passed into a combustion chamber (in our case, burning $CH_4$ in $O_2$), where it is heated to very high temperature. This heated, pressurised gas is then expanded and accelerated towards a turbine, which extracts its energy. The output temperature of the flue gas from this turbine is still high, and sufficient to provide heat for the steam turbine cycle. Combining these two cycles can be seen to increase the proportion of the heat generated by combustion of the fuel which is being put to use in electricity generation. Currently, efficiencies of 60% are common for CCGTs. As new materials and designs increase the maximum operating temperature of future-generation CCGTs, it can be expected that efficiencies will increase still further.

Combined cycle gas turbine electricity generators (CCGTEG) with and without District Heating are currently in frequent use burning fossil fuels such as natural gas. Gas is burned commonly with air and the gasses of combustion pass through the gas turbine doing work and producing electricity in the generator. Exhaust gases from the gas turbine then pass into a Rankine steam cycle boiler before being released to the atmosphere via the stack. Steam is formed in the boiler from the heat from the gas turbine exhaust gasses and then used to drive a steam turbine or turbines to produce further electricity. The steam is condensed to water before being returned to the boiler to continue the cycle. This normally occurs in a condenser or by use in District Heating. The present invention can use the CCGTEG in a possible manifestation.

Another, preferred, way of increasing the efficiency of the generating plant would be to run it as a Combined Heat and Power (CHP) system. In this format, the hot water (steam) from the outlet of the turbines would be used to provide district heating for the population of the area around the downstream plant. In this way, much of the 'waste heat' of a standard power plant can be recovered and put to use—efficiencies of over 80% are theoretically possible by this method.[15]

Existing Rankine Cycle electrical generating plants have an external water supply to make up losses from the steam cycle. The present invention would be able to supply make up water to the steam cycle of the CCGTEG. In the case where the Rankine cycle uses District Heating to condense its steam and provide water recovery, the system can be self-sustaining in water after plant start-up.

Heretofore, oxy-fuel use has been limited by the availability and cost of oxygen ($O_2$); for example oxygen extraction from the air would use 15% of the heat content of the fuel. The method specified, by obtaining oxygen directly from the upstream fuel/oxygen production plant, improves the prospects of oxy-fuel electricity generating plant.

The CCGTEG is typically fuelled by natural gas with air supported combustion where the gas turbine exhaust gasses pass into a Rankine steam cycle boiler before passing to atmosphere thereby releasing the $CO_2$ formed in combustion. The present invention will show how an oxy-fuel CCGTEG and associated plant can be designed to retain the $CO_2$ of combustion for reuse.

The near universal use of air to support combustion for electricity production has consequences if $CO_2$ extraction is desired because chemical extraction methods are necessary to separate the $CO_2$ from the nitrogen, of the combustion air, in the flue gasses. The present invention does not require chemical reaction methods for $CO_2$ extraction. In stipulating that hydrocarbon fuel combustion is supported with oxygen instead of air, the resultant exhaust gasses, $CO_2$ and $H_2O$, are then separable simply by cooling.

Another possible embodiment of the invention could use oxygen-methane electrolytic fuel cells with the option of district heating. The basic fuel cell envisaged would generate electricity by a well known electrochemical reaction when oxygen is passed continually over the cathode and hydrogen is passed over the anode, the hydrogen being derived from steam reforming of hydrogen from methane at temperatures around 760° C.

$$CH_4 + 2H_2O \Rightarrow CO_2 + 4H_2 \qquad \text{Steam Reforming:}$$

$$2H_2 \Rightarrow 4H^+ + 4e^- \qquad \text{Anode Reaction:}$$

$$O_2 + 4H^+ + 4e^- \Rightarrow 2H_2O \qquad \text{Cathode Reaction:}$$

$$2H_2 + O_2 \Rightarrow 2H_2O \qquad \text{Overall Cell Reaction:}$$

$$CH_4 + 2O_2 = CO_2 + 2H_2O \qquad \text{Overall Reaction:}$$

A hybrid of fuel cell and steam turbine design is also possible with the exhaust from the fuel cell being again $CO_2$ and steam, at 900° C., being used to drive the turbine generating further electricity. The exhaust from the turbine generator could go to district heating to achieve highly efficient energy transference. The fuels cells would not require the current standard desulphurisation methods essential with fossil fuels because of the complete absence of compounds of sulphur from the upstream plants. Moreover fuel cell life-time enhancement would be expected without the presence of such compounds.

Oxy-Fuel Combustion of $CH_4$

Several pilot projects have already been completed proving the feasibility of oxy-fuel combustion[16] and the adaptation of existing gas turbine technology to operate with oxy-fuel[17]. The biggest drawback has been identified as the cost in power of separating the required oxygen from air—estimated at 15% of the total generating capacity of the plant. As can be seen, our method bypasses this problem by obtaining $O_2$ from the electrolysis at the upstream thermo-gas-producing plant. In this way, we obtain a large efficiency saving in the downstream plant over existing oxy-fuel combustion projects.

The products of combustion of $CH_4$ in $O_2$ are just $CO_2$ and $H_2O$, summarised in the equation:

$$CH_4 + 2O_2 \rightarrow 2H_2O + CO_2$$

It can be seen that the greenhouse gas carbon dioxide is produced, just as in conventional hydrocarbon-burning power stations. However, the key advantage in using oxy-fuel combustion is that, after condensing out the water vapour, the resulting flue gas will be very pure (>95%) in $CO_2$, and will be without the nitrous oxides and sulphur dioxide resulting from combustion of impure coal or natural gas in air. This $CO_2$ will be cooled, before being transported back to the upstream plant (see below), for conversion to methane via the Sabatier process, as illustrated in FIG. 1.

Importantly, it should be realised that although $CO_2$ arises during the downstream process it will subsequently be consumed in the upstream process. Initially $CO_2$ from an external source is required to begin the thermogas production process but thereafter no new $CO_2$ is generated by the process.

The other product of the combustion reaction is $H_2O$, which can be put to use in several ways. A portion of the $H_2O$ produced by the reaction would be recycled in order to regulate the temperature at the gas turbine inlet, which would otherwise rise to levels requiring the use of very expensive and specially-designed materials in order to operate. The non-recycled remainder of the $H_2O$ holds interesting potential for commercial use. In the absence of pollutant impurities from the standard burning of fossil fuels in air, it could be treated with minerals and distributed as drinking water, or sold in bulk to nearby industries with a demand for pure demineralised water.

FIG. 5 shows a possible layout of the oxy-fuel CCGTEG plant. The fuel inlet stream 51 first passes through a pre-heater 53 where it takes heat from the $CO_2$ being returned through pipe 526 for transportation to the fuel production site. The heated fuel is then mixed with the $O_2$ inlet stream 52 and these are burned together in the combustion chamber 54 producing a high-temperature steam/$CO_2$ mixture 55 which expands through high-pressure gas turbine (HPT) 56 generating electricity in the electricity generator 526. This turbine will be constructed to the current industry-leading standard, and adapted for the high temperatures of oxy-fuel combustion using state-of-the-art materials. The outlet stream 57 from the HPT 56 then passes into a reheat combustor 58, where it is reheated to the inlet temperature of the Intermediate-Pressure Gas Turbine (IPT) 510 through combustion, using a portion of the fuel and oxygen streams diverted to reheat combustor 58 through pipes 530 and 531. This reheated stream 59 then expands through IPT 510 generating further power, and the exhaust stream 511 passes into a heat exchanger 512. Here, it gives up a portion of its heat to the recycled water 523 being used as an atemperator for combustion chamber 54. Such an atemperator is necessary since the burning of $CH_4$ in pure $O_2$ will generate extremely high flame temperatures, much higher than the optimal inlet temperatures of the HPT 56.

The steam/$CO_2$ mix then passes into the heat recovery steam generator 513, where it gives up its heat to the Rankine cycle boiler generating steam which passes through heat recovery steam generator 513 via banks of boiler tubes. This steam is then used to power steam turbine 515, generating further electricity. This turbine like turbine 56 will be constructed to the highest quality possible using well-defined, industry-accepted specifications. It is envisaged that the steam turbine outlet steam 516 can either be taken off for District Heating 517, or passed through a condenser 518 in order to prepare it for return as feed water to the heat recovery steam generator 513. In the case of District Heating, cool water will be returned through pipe 529 from the District Heating system, ensuring that the Rankine Cycle feed water is sustained.

In heat recovery steam generator 513, the steam/$CO_2$ mixture is separated by cooling. The $CO_2$ remains in the gas phase and is piped to $CO_2$ compressor 525, where it is compressed and then passed through pre-heater 53 before being taken off for return to the fuel/oxygen production site. The condensed water from heat recovery steam generator 513 is split into two parts: one part 519 can be taken off to water treatment facility still containing $CO_2$, while the other part 520 is fed into a degasser 521. From here, the $CO_2$ taken off 522 is fed back into heat recovery steam generator 513. Some of the degassed $H_2O$ is used as make-up to the feed water for the Rankine cycle steam generator 513. The remainder is split into two parts: $H_2O$ in pipe 523 is fed back through the heat exchanger 512 and then into combustion chamber 54 as an atemperator, while $H_2O$ in pipe 524 is taken off to the water treatment plant for export.

FIG. 6 shows a potential layout of the upstream fuel/oxygen production plant. $CO_2$ transported from the downstream CCGTEG plant enters the plant through pipe 61 and is heated to 205° C. by start-up heater 648 or by preheater 639 before joining with a stream of electrolysis-produced hydrogen 645 from pipe 643 and non-return valve 644. The combined stream 65, controlled at 205° C., then enters the Sabatier reactor tubes 66 (of which there are several, being fed by a manifold) where the $CO_2$ and $H_2$ react over a metal catalyst 67 to form $CH_4$ and $H_2O$. The metal catalyst would be the leading industrial standard for this reaction, currently Ru-doped $Al_2O_3$. The product stream of $CH_4$ and $H_2O$ passes through pipe 68 to a second heat exchanger 69, where the stream of $CH_4$ and $H_2O$ gives up part of its heat to the water in pipe 619. The $CH_4$ and $H_2O$ stream then passes through pipe 610 to condenser 612. A supply of cool water is fed into condenser 612 through pipe 611, cooling the mixture of $CH_4$ and $H_2O$ to the point where the $H_2O$ condenses to liquid water. The $CH_4$ leaves the condenser 612 through pipe 613, through which it passes to a $CO_2$ scrubber 614 used to remove any unreacted $CO_2$ from the Sabatier reactor tubes 66. The purified $CH_4$ is then taken off through pipe 615 for transportation to the downstream CCGTEG plant.

The Sabatier reaction needs a temperature of at least 200° C. to proceed and gives its highest product yield at around 300° C., above which increasing temperatures begin to favour the back reaction, reducing product yield and finally, at >500° C., stopping the forward reaction from occurring. The highly exothermic nature of the Sabatier reaction therefore means that, without temperature regulation, the reactor tubes would quickly heat to temperatures that would prevent a sustainable process. To prevent this, the cooled $H_2O$ 619 from condenser 612 is re-circulated to the main heat transfer reactor 625, where it is used as a heat transfer medium to maintain the Sabatier reactor tubes 66 at the optimal reaction temperature of 300° C., although some variance from 300° C. may be acceptable if it has benefits for other aspects of the system. In order to ensure the optimal steam conditions for injection into the heat transfer reactor 625, the $H_2O$ first passes through pipe 617 to heat exchanger 69, where it withdraws heat from the $CH_4/H_2O$ product stream as previously described, and then passes into a steam drum 620. For start-up electric heating 637 will be used. Steam from the steam drum 620 is used to heat the Sabatier reactor tubes 66, to a temperature of 205° C. As the $H_2O$ rises through heat transfer reactor 625 across the Sabatier reactor tubes 66, it is heated to 300° C. The steam continues to rise gaining heat by passing over successively tubes 641 and 642 containing the hot electrolysis products hydrogen and oxygen respectively. Further heating may also be applied by heater 653 for temperature control of the steam entering electrolysis cells 621.

The heated, high-pressure steam then passes into the electrolysis cells 621, illustrated in detail in FIG. 6a. The high-pressure superheated steam enters the cell at the cathode 621a. This is envisaged to be a solid-state electrode providing the best efficiency that current technology is capable of, at present a Ni—Zr cement. A DC electricity supply 621d generated from local renewable energy source (s) will drive the electrolysis of $H_2O$ into $H_2$ and $O_2$. The $H_2$ forms at the cathode 621a and is taken off through pipe connection 621e to pipe 622. The $O^{2-}$ ions migrate through the solid-state electrolyte 621b to the anode 621c, where they give up electrons and form $O_2$ molecules. Both the electrolyte and the anode will, like the cathode, reflect the optimal efficiencies available using current technology. At present, the electrolyte is envisaged to be yttria-stabilised zirconia, while the anode would be made from strontium-doped lanthanum manganite. At the anode, the $O_2$ produced is taken off through pipe connection 621f to pipe 626.

It is inevitable that sizable quantities of unreacted $H_2O$ will also enter the take-off connections 621a and thus pipe 622 and 624. The $H_2$ will therefore be separated from this steam in a separation chamber using a hydrogen-porous membrane 623. The $H_2$ will pass through the membrane and then enter pipe 62 and into the steam heating tubes 641 within the vessel 625 exiting via tube 63 into a Rankine cycle boiler 64 before joining the stream of $CO_2$ as previously described. The steam from the separation chamber 623 is passed back into the vessel 625 through a non-return valve 647 contained in tube 624 thereby to maintain the inlet steam to the electrolysis cells 621 at high temperatures approaching 900° C.

The electrolysis product oxygen exiting from collection manifold 626 is passed into the abovementioned steam heating tubes 642 within the vessel 625 then passing out to the collection manifold 627 and into a Rankine cycle boiler 628 to be cooled to approximately 30° C. as outgoing product at pipe 616.

The Rankine cycle boiler 64 heated by the hydrogen stream 63 has its boiler tubes fed from condensate water pipe 634. Steam is generated in the boiler 64, which passes to steam turbine 629 generating DC electricity in generator 633. In a similar manner, Rankine cycle boiler 628 heated by the oxygen stream 627 is fed by condensate 634 and raises steam for turbine 630 generating further electricity in the DC generator 633. Exhaust steam from the turbines 629 and 630 pass into condensers 631 and 632 respectively to form condensate in 634 to be pumped by feed pumps to boilers 64 and 628 to continue the Rankine cycle.

Yet further gains in efficiency can be achieved by the steam bridges 650 and 649 which connect to pipeline 651 feeding into the main heat transfer reactor 625. This would enable the reduction or elimination of Rankine condenser loss in condensers 631 and 632. The steam bridges 650 and 649 situated within steam turbines 629 and 630 contain valves to divert steam into pipeline 651 and to shut off steam flow to the low pressure side of the turbines 629 and 630. The high pressure side of turbines 629 and 630 would provide steam at 250 psi into the steam bridges, this being the pressure of saturated steam at the temperature required of 205° C. for inlet 625.

In order to pre-heat the $CO_2$ 61 entering the fuel/oxygen production process bled steam 638 from turbine 629 is passed to a heat exchanger 639. Condensate and low enthalpy steam is recovered from the heat exchanger 639 by pipe 640 and recovered into the condenser 631.

The DC generator 633 generates electricity to enable further electrolysis for further product production thereby to increase conversion of energy from the source energy (e.g. non-fossil source) to chemical energy in the methane and oxygen, potentially an efficiency of 70% or even higher, say 80% or even higher, with the additional heat recovery technologies described.

Thus it can be seen that the present invention provides a high efficiency combined electrolysis and Sabatier reaction apparatus and system. Excess heat produced during the Sabatier reaction is used to heat water that is then electrolysed. In order to further elevate the temperature of the water to be electrolysed, the high temperature outputs from the electrolysis process are passed though the water, which makes use of the high heat energy content of the electrolysis products to further raise the temperature of the water input. This increases overall efficiency of the electrolysis process. Furthermore, an additional potential loss of energy in the form of heat is avoided by using the still relatively hot oxygen and hydrogen, even after heating the electrolysis input water, to drive electricity generation via an additional generation stage, e.g. through a Rankine cycle. These features provide a highly efficient system for combining electrolysis and generation of methane. Of course, many of the efficiency increasing features can be used independently from each other, where appropriate, but the optimum efficiency is achieved where all the features are combined.

FIG. 9 shows a system for the transfer of energy from the grid by night into electricity and district heating by day being a possible embodiment of FIG. 1b. The system is characterised by having no emissions to atmosphere at the chosen location. Moreover when the generating assets supplying the grid through the night are independent of fossil fuels (e.g. renewable energy sources) there will be no resultant atmospheric emissions. However, in the general case where some or all of the assets supplying the grid use fossil fuels there will be $CO_2$ released at their respective source locations.

In FIG. 9 $CO_2$ from storage tank 960 passes through pipe 91 into start-up heater 948 and pre-heater 939, being heated to 205° C. The heated $CO_2$ 943 is lead through non-return valve 946 to meet a stream of electrolysis-produced hydrogen from pipe 92 and non-return valve 944. The hydrogen temperature is also 205° C. having been cooled in heat exchangers 941 and 94. The combined stream 95 is distributed by a manifold into numerous Sabatier tubes 96 contained within vessel 925 where the $CO_2$ and $H_2$ react over a metal catalyst 97 to form $CH_4$ and $H_2O$. The product stream of $CH_4$ and $H_2O$ is collected via an outlet manifold into pipe 98 and then passes into heat exchanger 99 where much of the heat generated by the Sabatier reaction passes into water tubes fed by supply pipe 919 to form steam in steam drum 920. The product stream reduced in temperature at outlet from heat exchanger 99 is led by pipe 910 to be cooled further in condenser 912 from which it exits to pipe 913 into $CO_2$ scrubber 914 which removes any unreacted $CO_2$ passing out from the Sabatier tubes 96. Steam formed in the Sabatier reaction is removed from the $CH_4$ by condenser 912 and the condensate passes into said pipe 919 to be pumped back into the said heat exchanger 99 to supply steam drum 920. The product $CH_4$ free of any steam or $CO_2$ is led by the said pipe 913 to be compressed by compressor 914 for storage by night in storage tank 962.

Water from storage tank 963 or demineralised from local sources 901 feeds cooling water to the said condenser 912 via supply pipe 903. After passing through condenser 912 the water joins with the condensate in said pipe 919.

Steam collects above the steam drum's controlled water level to supply steam at 205° C. to said heat exchanger vessel 925. The steam moves up through the vessel 925 and is heated, gaining in superheat, by the exothermic reaction of the Sabatier tubes 96, then further by hot hydrogen from the electrolysis in tubes 941 and then still further by hot oxygen from the electrolysis in tubes 942. A heater 953 is positioned above tubes 942 to enable further control of the steam temperature to be received by electrolysis cells 921.

Two further possible supplies of steam may be provided to vessel 925 in order to conserve heat in the process and minimise losses in converting electrical energy into chemical energy. During electrolysis some steam bypasses the cathode 921$e$ and is redirected back into vessel 925 via 924 and non-return valve 947 and secondly steam can be redirected into vessel 925 from steam bridges 958 and 959 situated within Rankine Cycle steam turbines 929 and 930. Turbines 929 and 930 use steam generated from heat exchangers 94 and 928 fed by the $H_2$ and $O_2$ streams subsequent to their exit from vessel 925.

The heated high pressure steam passes into electrolysis cells 921 which can receive rectified DC electricity from the grid and from generator 933 driven by the said turbines 929 and 930. $H_2$ produced at the cathode 121$e$ together with some steam passes out from collection manifold 922 into molecular filter vessel 928 which allows $H_2$ to pass into said tube 92 but diverts steam into said tube 924. $O_2$ is produced at the anode 121$f$ devoid of steam since the solid state electrolyte 121$b$ prevents the passage of gasses. The $O_2$ is collected at manifold 926 and is distributed by a further manifold into the said tube bank 942 being cooled in said vessel 925 and then is further cooled in heat exchanger 928 and led by pipe 916 to be compressed by compressor 964 into $O_2$ storage tank 961.

The said heat exchanger 928, heated by the $O_2$ stream 927, and the said heat exchanger 94, heated by the $H_2$ stream 93, contain Rankine Cycle boilers which take in feed water 934 and produce steam to steam lines 936 and 935 supplying steam to turbines 930 and 929. The turbines 930 and 929 connect to said DC generator 933 which supplies additional electricity to the electrolysis cells 121 having the effect of augmenting $CH_4$ and $O_2$ production.

Steam passes through turbines 930 and 929 into condensers 932 and 931 and the condensate is pumped into condensate lines 934 to continue the Rankine Steam Cycles in the said boilers 928 and 94. Demineralised make up 966 to the condensate lines 934 is provided. Steam turbine 929 provides bled steam 938 to said $CO_2$ pre-heater 939 which returns the outlet steam by pipe 940 to condenser 931.

The aforementioned steam bridges 959 and 958 situated within turbines 930 and 929 supply 250 psi steam at 205° C. through 951 to vessel 925 but can also provide optional district heating 956 which can supply steam through pipeline 954 and condensate returns through pipeline 955. During start-up, condensers 932 and 931 would be put into service then subsequently valves within the steam bridges would control the diversion of steam to pipe 951 and the partial or complete shut off of steam to the condensers.

Thus $O_2$ and $CH_4$ collect in storage tanks 961 and 962 by night, to enable electricity supply to the grid and heat energy to district heating, during day, by the plant described below.

$O_2$ from said storage tank 961 and $CH_4$ from storage tank 962 are led by pipes 968 and 969 to combustion chamber 976 and also by pipes 982 and 983 to reheat combustor 977. $CH_4$ burns in $O_2$ in the said combustion chamber 976 and being attemperated by cooling water 988 issues out as $CO_2$ and steam into high pressure gas turbine 972. This working fluid powers turbine 972 and exhausts via 984 and is used as attemperator fluid for said reheat combustor 977. Further $CH_4$ burns in $O_2$ in said reheat combustor 977 and is, after being attemperated by said stream 984, directed by pipe 985 into intermediate pressure gas turbine 973 to power the turbine. Turbine 973 exhausts $CO_2$ and steam via 989 into heat exchanger 957 and then into vessel 978. Vessel 978 functions as a $CO_2$ and $H_2O$ separator being a heat exchanger containing boiler tubes fed cool water 995. The hot $CO_2$ and $H_2O$ passing down through vessel 978 generate steam in the boiler tubes 943 being successively cooled in the process until the water condenses. The $CO_2$ is lead off by pipeline 999 to compressor 971 and recovered by pipe 967 into storage tank 960 to accumulate during the day. The water falls to the well of vessel 978 and into drain 990 when, still containing $CO_2$ in solution, is led into degasser 981. Mechanical agitators in the degasser 981 separate the $CO_2$ from the water. The separated $CO_2$ is passed back by pipe 991 to vessel 978.

Water passes from the degasser 981 to provide make up to the boiler feed water 995 pumped into the Rankine Cycle said boiler tubes 943 contained in said vessel 978. Steam generated in boiler tubes 943 passes into steam turbine 974 via steam pipeline 979. Steam turbine 974 together with said high pressure gas turbine 972 and said intermediate pressure gas turbine 973 drive said compressor 971 and also electricity generator 975. Electricity generator 975 supplies electricity to the grid by day. Steam exhausts from steam turbine 974 into condenser 996 or is diverted in whole or in part to district heating supply 993. Condensate 980 from condenser 996 meets with water returning from district heating 994 to provide boiler feed water in feed pipe 995 to said boiler tubes 943 to continue the Rankine Cycle.

Water from the degasser 981 passes into pipe 986 and a portion taken into pipe 987 to be pumped through tubes in the said heat exchanger 957 as the atemperator coolant 988 to said combustion chamber 976. The remaining portion of water from pipe 986 is fed into pipeline 970 which leads into storage tank 963.

Thus $CO_2$ and water collect in storage tanks 960 and 963 by day to enable the production of $O_2$ and $CH_4$ by night to continue time-phased energy transference.

Production of Methane Derivatives

While the methane produced by the Sabatier reactors represents the basic thermogas, this need not be the only useful product gas obtained from the upstream plant. Indeed, significant research is currently underway aiming to make commercially feasible the conversion of methane into a multitude of alternative chemical feedstock gases. Two significant examples are ethylene, $C_2H_4$, and longer-chain hydrocarbons.

The manufacture of ethylene (and other $C_2+$ hydrocarbons) from oxidative coupling of methane has been known for decades, with its reactants the very gases produced in our upscale plant: $CH_4$ and $O_2$. Until recently, efforts to make the process economically feasible had stalled: a seemingly unavoidable trade-off between catalyst efficiency and product selectivity limited the yield to levels well below those commercially viable.[9] However, new developments in reactor technology and porous nanomolecule catalysts have re-raised the possibility of this process being developed into a commercial route to ethylene manufacture. Indeed, the OCMOL project[10] has recently been given substantial funding by the European Union to carry out an extensive five-year project pursuing this aim.

The manufacture of larger-chain hydrocarbons from a methane feedstock has also attracted considerable interest in recent years. For example, WiesnerTech have submitted a patent application for one method of doing this.[11] In many ways their proposed plant set-up resembles the upstream plant we are proposing. In their scheme, the $CH_4$ produced by the Sabatier reactor would be fed into a partial oxidation reactor, and the output gases then fed into Fischer-Tropsch reactor, in order to create longer-chain hydrocarbons by a well-known process,[12] which would then be separated and exported to market.

Such developments as those mentioned above can be seen to be entirely compatible with, and in fact complementary to, the scheme we are here proposing, and could evidently be integrated into the upstream plant, providing the capacity for manufacture of a whole range of useful fuels and chemicals some of which are shown in FIG. 8.

CONCLUSIONS

At present less than 2% of the world's electricity demand is met by emissions free renewable energies. This is despite the capacity for generating electricity from such sources being very large indeed. The present invention will enable extensive large scale development of these renewable non-$CO_2$-emitting energies, e.g. hydro, solar, geothermal, wind, tidal currents, nuclear and others for reliable electricity supply, without the necessity of a direct local connection to the electricity grid. Upon widespread adoption of the invention, the energy sources are sufficiently large as to completely replace fossil fuels for electricity supply. This in turn will enable world economic growth to continue to rise without atmospheric $CO_2$ levels rising due to electricity supply.

Furthermore the present invention opens new opportunities to improve the ability of the current generation systems to meet changing levels of demand and to provide chemical feedstock for industrial processes.

The invention can be seen to have several potentially significant benefits. These can be categorised as environmental or economic benefits, as described below.
Environmental Benefits The principal environmental benefit of the approach advocated in this application (and, indeed, one of the main driving factors for its development) is the potential for the complete absence of any $CO_2$ emissions to the atmosphere, despite the use of relatively cheap and well-established gas-turbine generation methods to ensure a reliable electricity supply. A 2008 European Environmental Agency (EEA) report[20] estimated that 56.1 kg of $CO_2$ was emitted to the atmosphere for every gigajoule (GJ) of energy generated by the combustion of natural gas. This corresponds to over 200 tonnes of $CO_2$ per hour for every 1 GW CCGT plant. Moreover, natural gas is generally considered the 'cleanest' fossil fuel for combustion—rates of emission per gigajoule generation for oil, and especially coal, are estimated to be much higher. Therefore, the idea detailed in this application clearly could lead to a dramatic reduction in $CO_2$ emissions if implemented on a large scale, essentially facilitating the harnessing of the vast quantities of renewable energy available across the globe in a reliable way. In addition, or in the alternative the present invention provides a method by which excess electricity can be captured and stored for later use (in the form of chemical energy), without the emission of any $CO_2$.

As an example, consider the Pentland Firth, situated to the north of Scotland, between the British mainland and the Orkney Islands. This channel of water is well-known for its quick and powerful tidal runs, and accordingly has been the subject of much interest for years due, to its potential for electricity generation by underwater turbines. Previous estimates using a very simplified model[21] suggest that the seabed dissipation as the water passes through the channel at its maximum velocity is on the scale of 50 GW. A single full bank of turbines across the 10 km width of the channel could have a potential generating capacity of nearly 15 GW at times of peak tidal power. Clearly, the ability to harness even half of this power would enable electricity generation for the whole of Scotland.

The total power a continuous flow of water travelling with a velocity v, across a width W and depth Z is given by:

$$P = \frac{1}{2} \cdot \rho \cdot W \cdot Z \cdot v^3$$

It can therefore be seen that any potential for increasing the velocity of the water would mean far greater power generation capability. For example, consider halving the 80 m depth of the Pentland Firth at the turbine site. The velocity would double accordingly to ensure the flow rate remained constant. However the power per unit volume of the water would have quadrupled, as this is dependent on $v^3$ but only linearly on Z.

However, the tidal runs, while predictable, do not always conveniently correspond to the times of peak electricity demand—often, they will occur in the middle of the night. The method of this paper would provide an effective means to 'make hay while the sun shines': the huge maximum generation capacity at times of peak tidal power could be converted into $CH_4$ and $O_2$ stocks, which would then be transported downstream to generating plant for combustion to fire CCGTs to meet demand.

Another powerful example is the case of wind turbine generation. The wind contains great amounts of potential power, but is notoriously unpredictable and therefore unreliable, which has limited its usefulness as a large-scale alternative to fossil fuels. Converting the energy provided by wind turbines into thermogas and oxygen for storage and subsequent downstream generation would enable this difficulty to be effectively overcome. This would greatly increase the viability of large-scale wind turbine projects as a credible alternative to fossil fuel combustion, to meet a significant proportion of overall electricity demand.

To combat the rising environmental and associated economic costs of large-scale $CO_2$ emissions, the fossil fuel industry is currently investing large sums of money into the development of various 'carbon capture' methods. These essentially involve retrieving the $CO_2$ from the flue gases at fossil fuel-fired power plants and transporting it for sequestration. This is a difficult and expensive process, however, driving up the operating costs of the plant and reducing profitability; this has prompted the recent research into oxy-fuel combustion, which gives a far cleaner and more readily-separated flue gas mixture as described previously.

The biggest drawback of oxy-fuel combustion methods in their current incarnation is the difficulty of separating the desired oxygen from air, which requires so much energy as to cripple the overall generating capacity of the plant. Furthermore, regardless of the method of carbon-capture used, it is far from certain that $CO_2$, once sequestered, will remain so in the long term, and not begin to leak to the atmosphere. The methods we propose provide a very elegant solution to this two-fold problem. On the one hand, the $O_2$ produced during the electrolysis of $H_2O$ at the upstream plant is transported and used at the oxy-fuel combustion stage, removing the need for separation from air. Meanwhile, the $CO_2$ produced, easily separated from the flue gas mixture due to the use of oxy-fuel combustion, is transported back to the upstream plant for use in the Sabatier reactors to generate more $CH_4$.

An additional environmental benefit is provided by virtue of the fact that the thermogas would be a manufactured commodity, and therefore would contain almost none of the impurities which are found in geologically-bound fossil fuels. This means that the flue gases from the CCGT combustion would be much 'cleaner', containing none of the unpleasant and polluting nitrogen oxides (NOx) or sulphur dioxide ($SO_2$) which generally result from the burning of fossil fuels, particularly coal. The EEA estimates that at present, over a kilogram of $SO_2$ is emitted for every gigajoule of energy generated by coal and oil-fired power plants—this corresponds to nearly five tonnes an hour for a 1 GW CCGT plant. Currently, such plants may be releasing anything up to a tonne of NOx an hour, with a substantial percentage of this being $NO_2$, a gas toxic to humans and a major atmospheric pollutant. $SO_2$ is also known to be an atmospheric pollutant, and a precursor for acid rain. Eliminating such substantial emissions to atmosphere of these and similar undesirable compounds is therefore a great environmental benefit of our proposed system.

Economic Benefits

In addition to the environmental benefits outlined above, the method we are proposing holds several key economic advantages when compared to similar schemes being piloted or currently in operation. Many of these arise as a natural consequence of the cyclic nature of the process, with comprehensive re-use of materials wherever possible.

The most obvious advantages again lie in the capture and re-use of $CO_2$ from combustion, and resultant lack of $CO_2$ emissions to the atmosphere. In addition to the obvious environmental advantages, this can equally be viewed in terms of its potential economic benefits. Across the world, there is a growing trend among governments towards imposing sizeable per-tonne levies on emissions of $CO_2$, which will push the cost of operating conventional fossil-fuel power plants ever upward.[22] In addition to the increasing levies on $CO_2$ emissions, the cost of obtaining fossil fuels from geological formations will continue to rise. Increasingly challenging environments need to be accessed and manipulated, at depths and pressures which require greater feats of engineering and hold more potential for disaster. Political factors may also come into play: large amounts of the remaining known oil and gas reserves may lie within states governed by unfriendly or openly hostile regimes, jeopardising a nation's future energy supply. The combination of these factors will make generation from alternative energy sources an increasingly attractive option, provided they can be usefully and reliably harnessed.

Our approach thus should enable the energy industry to invest heavily in large-scale development of renewable resources with an increased measure of confidence. Furthermore, much of the technology required is already well-understood, and energy companies have the expertise in operating it. CCGTs, pipeline construction and operation, and ship tanker transportation are all well-developed methods which have been in extensive use for decades. The existing gas grid could even potentially be modified in order to transport some or all of the process gases required, potentially leading to large savings over the cost of constructing a new network from scratch.

Another major advantage lies in the potential for a universal, standardised design of downstream generating plant, varying only in scale, with a range of turbine sizes (power ratings) possible, but with the plant design always to the same blueprint. This would replace the current multifarious plant designs, required at present due to the range of different fuels burned. Thus, comprehensive research and development efforts could more easily be focused both on optimising the efficiency, and on minimising the construction and operating costs of this single standard design. It could therefore be expected that the cost and build-time of new CCGT generating plant or other suitable plants would decrease substantially over time.

Similarly, there is substantial potential for improving the cost-efficiency of the upstream plant processes. Any improvement in the efficiency of the electrolysis of $H_2O$, which provides both the $O_2$ for combustion and the $H_2$ for the Sabatier reaction, would be most beneficial. Thanks to its potential as a simple route to the materials $H_2$ and $O_2$, which have a multitude of uses, much research is indeed focused on improving this reaction,[25,26] with the development of solid-state electrolysers and research into high-temperature electrolysis two notable recent developments.

Due to its cyclic nature, an increased efficiency in the downstream section of the process will correspond to a large improvement in overall efficiency. For example, an increase in oxy-fuel CCGT efficiency from 60% to 65% would correspond to nearly an 8% reduction in the required amounts of $CH_4$ and $O_2$, meaning a corresponding reduction in the quantity of water needing to be electrolysed, and an increase in downstream/upstream generation efficiency of 15% or more. As the technology of oxy-fuel combustion is still in its infancy, the potential clearly exists for substantial improvements to be developed, particularly if major research were to be devoted to this, as would inevitably occur should the idea proposed here gain widespread support.

A further key benefit is provided by the flexibility of the method, and in particular the sites of the upstream and downstream sections of plant. These could be hundreds of miles apart, with a pipeline and ship tanker transportation network connecting them. In this case, thermogas and $O_2$ would be generated directly from the alternative energy source at the upstream site, and transported to the downstream plant. Here, they would be stored in large tanks until required for combustion at times of high electricity demand. This set-up would enable the siting of downstream plant close to areas of high local electricity demand, enabling generation local to the point of demand as and when required. Construction of the downstream plant close to population centres would furthermore facilitate a CHP setup as described above providing district heating to the local population directly from the steam output and thereby achieving considerably higher efficiencies than those of the CCGT generation-only plant.

As an alternative, particularly where the renewable energy generation site was not particularly far from a population centre or attached to the national grid, the upstream and downstream sections of plant could be integrated at a single site. This would have the considerable economic advantage of bypassing nearly all of the transportation costs, requiring only reduced-scale pipeline construction, along with the capacity to store the levels of thermogas and $O_2$ produced at peak production times until their use at times of peak electricity demand.

Furthermore, the methods of synthesis described herein provide alternative routes to petrochemicals allowing the replacement of conventional fossil fuel sources. These can be achieved in a manner which allows control of $CO_2$ emissions. Petrochemical feed stocks to make polymeric materials and other such products can be achieved via synthesis as described above, e.g. from alternative energy sources, and this can actually result in the fixing of $CO_2$ from which they are made. Upon eventual disposal, e.g. in landfill, the $CO_2$ would be essentially permanently fixed. Fuels required for transport could be reduced by a partial shift to emissions free electricity, rail transport being the most obvious exponent for ready adoption of such energy. Transportation having large power units, such as shipping, could be adapted for oxy-fuel combustion to recover their exhaust $CO_2$ in an analogous manner to that described above, i.e. cooling exhaust gases to separate $CO_2$ from water. Such $CO_2$ could be returned for further thermogas production, potentially in return for payment. Potentially even small power units, such those in cars, could be converted for oxy-fuel combustion with subsequent $CO_2$ recovery, though the increased capital cost would be a disincentive. Power units that continue to use air for combustion, including aviation jet engines, could have a supplemental cost added to fuel in order to fund extraction of $CO_2$ by means of renewable energies.

Thus, in summary, practical methods are made possible of preventing the escalating global $CO_2$ emissions driven by mankind.

Summary and Future Work

Methods and apparatus by which electricity can be generated reliably and flexibly from alternative energy sources, without emission of $CO_2$ or sulphurous and nitrogenous pollutants to the atmosphere, via the production and subsequent combustion of gas as an energy storage medium have been described. Aspects of the invention can be combined in an elegant and efficient cyclic process with few waste products, thanks to the use of oxy-fuel combustion in the CCGT generation plant or using fuel cell technology. We believe that the approach outlined here, if implemented in tandem with large-scale development of renewable energy resources, have the potential to greatly reduce our dependence on fossil fuels for electricity generation. Further development work is now required in order to refine and optimise the invention.

REFERENCES

1. Siemens Energy: Clean Energy Systems, *Oxyfuel turbine development overview*, 2008.
2. Haile, S., appearance on The Science Show (Australia), *Using solar power to produce non-fossil liquid fuels for transportation*, 2011.
3. Hashimoto, K., Global carbon dioxide recycling, 2006. http://www15.ocn.ne.jp/~hashico2/
4. www.en.wikipedia.org/wiki/Sabatier_reaction
5. Richardson, J., *Improved Sabatier reactions for in situ resource utilisation on Mars missions*, 2008.
6. Richardson, J., *Advanced catalysts and reactors for Mars exploration Sabatier processors*, 2001.
7. Chao, C-C.; Kim, Y. B.; Prinz, F. B., *Surface modification of Yttria-stabilised Zirconia electrolyte by atomic layer deposition*, Nano Lett., 2009, 9(10), pp. 3626-3628.
8. Doctor, R.; Matonis, D.; Lyczkowski, R. (Argonne National Laboratory), *notes from DOE Solar hydrogen workshop*, 2004.
9. Jaso, S.; Godini, H. R.; Arellano-Garcia, H.; Wozny, G. *Oxidative coupling of methane: reactor performance and operating conditions*, $20^{th}$ European symposium on computer-aided process engineering, 2010.
10. www.ocmol.eu.
11. Wiesner, B. L., *Method of combining existing chemical processes to produce hydrocarbon fuels*, U.S. patent application Ser. No. 12/547,347.
12. Dry, M. E., *The Fischer-Tropsch process: 1950-2000*, Catalysis Today, 2002, 71, 3-4, pp. 227-241.
13. www.carringtonpower.co.uk/technology
14. www.eon-uk.com/generation/drakelowccgt.aspx
15. Combined Heat and Power Association, www.chpa.org
16. *R&D facts: Oxy-fuel combustion*, U.S. Department of Energy, Office of Fossil Energy, National Energy Technology Laboratory, 2008.
17. Anderson, R. E.; MacAdam, S.; Viteri, F.; Davies, D. O.; Downs, J. P.; Paliszewski, R. *Adapting gas turbines to zero emission oxy-fuel power plants*, Proceedings of AMSO turbo expo., 2008.
18. Article: *Samsung to deliver world's biggest LNG tanker for Exxon project*, Bloomberg, 2008.
19. Asia Industrial Gases Association (AIGA), *Oxygen pipeline systems* (*globally harmonised document AIGA 021/05*), 2005.
20. *Air pollution from electricity-generating large combustion plants*, Copenhagen: EEA, 2008, ISBN 978-92-9167-355-1.
21. Salter, S. H.; Taylor, J. R. M., *Vertical-axis tidal-current generators and the Pentland Firth*, Proc. IMechE. 221 Part A: J. Power and Energy 295, 2006.
22. P B Power, *The cost of generating electricity—a commentary on a study carried out for the Royal Academy of Engineering*, 2004.

The invention claimed is:

1. A method for producing a hydrocarbon or a hydrocarbon derivative from an electrical energy source, said method comprising:
   a. providing a source of electrical energy;
   b. using electrical energy from said source to electrolyse water to form hydrogen and oxygen; and
   c. using hydrogen thereby formed to hydrogenate carbon dioxide to form methane; and
   wherein the electrolysis is carried out at a temperature of from 100° C. to 1000° C., wherein heat produced by the hydrogenation of carbon dioxide is used to heat the electrolysis reaction, wherein heat in the stream of hydrogen and/or oxygen produced in electrolysis is used to generate steam, and wherein the steam produced is used to generate electricity.

2. A system for producing a hydrocarbon or a hydrocarbon derivative from an electrical energy source, said system comprising:
   a) a source of electrical energy;
   b) an electrolysis apparatus electrically coupled to said energy source operable to electrolyse water to form hydrogen and oxygen;
   c) gas handling means to collect oxygen and hydrogen produced in said electrolysis apparatus;
   d) a source of carbon dioxide; and
   e) a hydrogenation apparatus adapted to hydrogenate carbon dioxide to form methane using said hydrogen produced by electrolysis; and
   wherein the electrolysis apparatus and the hydrogenation apparatus contain heating means and cooling means respectively, and the heating means of the electrolysis apparatus and the cooling means of the hydrogenation apparatus are thermally coupled such that heat energy generated in hydrogenation can be transferred to the electrolysis apparatus, wherein the system is adapted such that the flow of hydrogen and/or oxygen from the electrolysis apparatus is used to generate steam in a boiler, and wherein further the system comprises a steam generator adapted to generate electricity from said steam.

3. A system for producing a hydrocarbon or a hydrocarbon derivative from an electrical energy source, said system comprising:
   a) a source of electrical energy;
   b) an electrolysis apparatus electrically coupled to said energy source operable to electrolyse water to form hydrogen and oxygen;
   c) gas handling means to collect oxygen and hydrogen produced in said electrolysis apparatus;
   d) a source of carbon dioxide; and
   e) a hydrogenation apparatus adapted to hydrogenate carbon dioxide to form methane using said hydrogen produced by electrolysis; and
   wherein the electrolysis apparatus and the hydrogenation apparatus contain heating means and cooling means respectively, and the heating means of the electrolysis apparatus and the cooling means of the hydrogenation apparatus are thermally coupled such that heat energy generated in hydrogenation can be transferred to the electrolysis apparatus, wherein the system is adapted such that the flow of hydrogen and/or oxygen from the electrolysis apparatus is used to generate steam in a boiler, wherein the system is further adapted such that the steam can be fed back into a flow of input water for electrolysis, and the system further comprising at least one steam bridge operable to selectively direct steam through a steam turbine or direct the steam from the high pressure side of the steam turbine to a flow of input water for electrolysis.

4. A combined electrolysis/hydrogenation apparatus for use in the generation of methane and performing electrolysis of water comprising:
   a high temperature electrolysis apparatus adapted for electrical coupling to a source of electrical energy, said high temperature electrolysis apparatus being operable to electrolyse water at high temperature in an electrolysis chamber using electrical energy from said source to form hydrogen and oxygen, the high temperature electrolysis apparatus comprising an input water feed conduit adapted to carry water to the site of electrolysis;
   gas handling means to collect oxygen and hydrogen produced in said electrolysis apparatus comprising gas-carrying conduits adapted to carry the oxygen and hydrogen;
   a hydrogenation apparatus adapted to hydrogenate carbon dioxide to form methane using said hydrogen produced in the high temperature electrolysis apparatus comprising a hydrogenation chamber in which hydrogenation of carbon dioxide occurs; and
   at least one steam bridge operable to selectively direct steam through a steam turbine or direct the steam from the high pressure side of the steam turbine to the feed conduit of input water for electrolysis;
   wherein at least a portion of the hydrogenation apparatus is in thermal communication with the feed conduit, such that heat generated in the hydrogenation reaction can heat water to be electrolysed.

* * * * *